United States Patent
Nastri et al.

(10) Patent No.: US 11,884,724 B2
(45) Date of Patent: *Jan. 30, 2024

(54) ANTI-PD-L1 ANTIBODIES AND USES THEREOF

(71) Applicant: Merck Patent GmbH, Darmstadt (DE)

(72) Inventors: Horacio G. Nastri, Needham, MA (US); Christel Iffland, Cambridge, MA (US); Olivier Leger, Saint-Sixt (FR); Qi An, Nashua, NH (US); Mark Cartwright, West Newton, MA (US); Sean D. McKenna, Duxbury, MA (US)

(73) Assignee: Merck Patent GmbH, Darmstadt (DE)

( * ) Notice: Subject to any disclaimer, the term of this patent is extended or adjusted under 35 U.S.C. 154(b) by 652 days.

This patent is subject to a terminal disclaimer.

(21) Appl. No.: 16/984,365

(22) Filed: Aug. 4, 2020

(65) Prior Publication Data

US 2021/0054073 A1    Feb. 25, 2021

Related U.S. Application Data

(60) Continuation of application No. 15/454,939, filed on Mar. 9, 2017, now Pat. No. 10,759,856, which is a division of application No. 14/360,775, filed as application No. PCT/EP2012/004822 on Nov. 21, 2012, now Pat. No. 9,624,298.

(60) Provisional application No. 61/563,903, filed on Nov. 28, 2011.

(51) Int. Cl.
| | |
|---|---|
| *C07K 16/28* | (2006.01) |
| *A61K 45/06* | (2006.01) |
| *A61K 31/555* | (2006.01) |
| *A61K 39/395* | (2006.01) |
| *A61K 31/675* | (2006.01) |
| *A61K 31/7068* | (2006.01) |
| *A61K 39/00* | (2006.01) |
| *A61K 31/282* | (2006.01) |
| *A61K 31/513* | (2006.01) |
| *A61K 31/519* | (2006.01) |

(52) U.S. Cl.
CPC ........ *C07K 16/2803* (2013.01); *A61K 31/282* (2013.01); *A61K 31/513* (2013.01); *A61K 31/519* (2013.01); *A61K 31/555* (2013.01); *A61K 31/675* (2013.01); *A61K 31/7068* (2013.01); *A61K 39/001102* (2018.08); *A61K 39/3955* (2013.01); *A61K 39/39558* (2013.01); *A61K 39/39591* (2013.01); *A61K 45/06* (2013.01); *C07K 16/2827* (2013.01); *A61K 2039/505* (2013.01); *C07K 2317/34* (2013.01); *C07K 2317/55* (2013.01); *C07K 2317/56* (2013.01); *C07K 2317/73* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,794,710 | B2 | 9/2010 | Chen et al. |
| 7,943,743 | B2 | 5/2011 | Korman et al. |
| 8,217,149 | B2 | 7/2012 | Irving et al. |
| 9,102,725 | B2 | 8/2015 | Korman et al. |
| 9,624,298 | B2 | 4/2017 | Nastri et al. |
| 10,487,147 | B2 | 11/2019 | Nastri et al. |
| 10,759,856 | B2 | 9/2020 | Nastri et al. |
| 2008/0213251 | A1 | 9/2008 | Sexton et al. |
| 2009/0055944 | A1 | 2/2009 | Korman et al. |
| 2010/0086550 | A1 | 4/2010 | Kang et al. |
| 2010/0203056 | A1 | 8/2010 | Irving et al. |
| 2011/0271358 | A1 | 11/2011 | Freeman et al. |
| 2013/0034559 | A1 | 2/2013 | Queva et al. |
| 2014/0302060 | A1 | 10/2014 | Beg et al. |
| 2018/0169232 | A1 | 6/2018 | Andrews et al. |
| 2018/0244781 | A1 | 8/2018 | Cuillerot et al. |
| 2018/0282415 | A1 | 10/2018 | Lin et al. |
| 2018/0369377 | A1 | 12/2018 | Rinaldi et al. |
| 2019/0144545 | A1 | 5/2019 | Nuyten et al. |

FOREIGN PATENT DOCUMENTS

| | | |
|---|---|---|
| EP | 1537878 A1 | 6/2005 |
| WO | WO-2001/014557 A1 | 3/2001 |
| WO | WO-2002/086083 A2 | 10/2002 |
| WO | WO-2007/005874 A2 | 1/2007 |
| WO | WO-2008/083174 A2 | 7/2008 |
| WO | WO-2010/036959 A2 | 4/2010 |
| WO | WO-2010/077634 A1 | 7/2010 |
| WO | WO-2011/066389 A1 | 6/2011 |

OTHER PUBLICATIONS

Blank C et al., (2006), Blockade of PD-L1 (B7-H1) Augments Human Tumor-Specific T Cell Responses in vitro, Int J Cancer, 119(2):317-27.

Boettler T et al., (2006), 'Expression of the Interleukin-7 Receptor Alpha Chain (CD127) on Virus-Specific CD8+ T Cells Identifies Functionally and Phenotypically Defined Memory T Cells During Acute Resolving Hepatitis B Virus Infection,' J Virol, 80(7):3532-40.

Bullock AN et al., (1997), 'Thermodynamic Stability of Wild-Type and Mutant p53 Core Domain,' Proc Natl Acad Sci USA, 94(26):14338-42.

Butte MJ et al., (2007), 'Programmed Death-1 Ligand 1 Interacts Specifically with the B7-1 Costimulatory Molecule to Inhibit T Cell Responses,' Immunity, 27(1):111-22.

(Continued)

*Primary Examiner* — Ilia I Ouspenski
(74) *Attorney, Agent, or Firm* — Goodwin Procter LLP

(57) ABSTRACT

The present application relates to anti-PD-L1 antibodies or antigen binding fragments thereof, nucleic acid encoding the same, therapeutic compositions thereof, and their use to enhance T-cell function to upregulate cell-mediated immune responses and for the treatment of T cell dysfunctional disorders, such as tumor immunity, for the treatment of and cancer.

14 Claims, 8 Drawing Sheets

Specification includes a Sequence Listing.

(56) References Cited

OTHER PUBLICATIONS

Carter L et al., (2002), 'PD-1:PD-L Inhibitory Pathway Affects Both CD4(+) and CD8(+) T Cells and is Overcome by IL-2,' Eur J Immunol, 32(3):634-43.
Corthay A, (2009), 'How do Regulatory T Cells Work?,' Scand J Immunol, 70(4):326-36.
Dong H et al., (1999), 'B7-H1, a Third Member of the B7 Family, Co-Stimulates T-Cell Proliferation and Interleukin-10 Secretion,' Nat Med, 5(12):1365-9.
Dong H et al., (2002), 'Tumor-Associated B7-H1 Promotes T-cell Apoptosis: A Potential Mechanism of Immune Evasion,' Nat Med, 8(8):793-800.
Eppihimer MJ et al., (2002), 'Expression and Regulation of the PD-L1 Immunoinhibitory Molecule on Microvascular Endothelial Cells,' Microcirculation, 9(2):133-45.
Francisco LM et al., (2010), 'The PD-1 Pathway in Tolerance and Autoimmunity,' Immunol Rev, 236:219-42.
Freeman GJ et al., (2000), 'Engagement of the PD-1 Immunoinhibitory Receptor by Novel B7 Family Member Leads to Negative Regulation of Lymphocyte Activation,' J Exp Med, 192(7):1027-34.
Goldberg MV et al., (2007), 'Role of PD-1 and its Ligand, B7-H1, in Early Fate Decisions of CD8 T Cells,' Blood, 110(1):186-92.
Heckman KL et al., (2007), 'Fast-Tracked CTL: Rapid Induction of Potent Anti-Tumor Killer T Cells in situ,' Eur J Immunol, 37(7):1827-35 (Retracted in 2010).
Holt LJ et al., (2003), 'Domain Antibodies: Proteins for Therapy,' Trends Biotechnol, 21(11):484-90.
International Search Report for PCT/EP2012/004822 dated Mar. 1, 2013.
Iwai Y et al., (2002), 'Involvement of PD-L1 on Tumor Cells in the Escape from Host Immune System and Tumor Immunotherapy by PD-L1 Blockade,' Proc Natl Acad Sci USA, 99(19):12293-7.
Keir ME et al., (2008), 'PD-1 and its Ligands in Tolerance and Immunity,' Annu Rev Immunol, 26:677-704.
Kuipers H et al., (2006), 'Contribution of the PD-1 Ligands/PD-1 Signaling Pathway to Dendritic Cell-Mediated CD4+ T Cell Activation,' Eur J Immunol, 36(9):2472-82.
Latchman YE et al., (2001), 'PD-L2 is a Second Ligand for PD-1 and Inhibits T Cell Activation,' Nat Immunol, 2(3):261-8.
Latchman YE et al., (2004), 'PD-L1-Deficient Mice Show that the PD-L1 on T Cells, Antigen-Presenting Cells, and Host Tissues Negatively Regulates T Cells,' Proc Natl Acad Sci, USA, 101(29):10691-6.
Lee SJ et al., (2006), 'Interferon Regulatory Factor-1 is Prerequisite to the Constitutive Expression and INF-γ-Induced Upregulation of B7-H1 (CD274),' FEBS Lett, 580(3):755-62.
Liang SC et al., (2003), 'Regulation of PD-1, PD-L1, and PD-L2 Expression During Normal and Autoimmune Responses,' Eur J Immunol, 33(10):2706-16.
Liu et al., (2016), "Structural Basis of anti-PD-L1 monoclonal antibody avelumab for tumor therapy," Cell Res., 27(1):151-153.
Liu J et al., (2007), 'Plasma Cells from Multiple Myeloma Patients Express B7-H1 (PD-L1) and Increase Expression After Stimulation with INF-γ and TLR Ligands via a MyD88-, TRAF6-, and MEK-Dependent Pathway,' Blood, 110(1):296-304.
Loke P and Allison JP, (2003), 'PD-L1 and PD-L2 are Differentially Regulated by Th1 and Th2 Cells,' Proc Natl Acad Sci USA, 100(9):5336-41.
Nguyen LT et al., (2002), 'Cross-Linking the B7 Family Molecule B7-DC Directly Activates Immune Functions of Dendritic Cells,' J Exp Med, 196(10):1393-8 (Retracted on Apr. 5, 2010).
Nielsen C et al., (2005), 'Alternative Splice Variants of the Human PD-1 Gene,' Cell Immunol, 235(2):109-16.
Nishimura H et al., (1996), 'Developmentally Regulated Expression of the PD-1 Protein on the Surface of Double-Negative (CD4-CD8-) Thymocytes,' Int Immunol, 8(5):773-80.
Nishimura H et al., (1999), 'Development of Lupus-Like Autoimmune Diseases by Disruption of the PD-1 Gene Encoding an ITIM Motif-Carrying Immunorecptor,' Immunity, 11(2):141-51.
Nishimura H et al., (2001), 'Autoimmune Dilated Cardiomyopathy in PD-1 Receptor-Deficient Mice,' Science, 291(5502):319-22.
Nomi T et al., (2007), 'Clinical Significance and Therapeutic Potential of the Programmed Death-1 Ligand/Programmed Death-1 Pathway in Human Pancreatic Cancer,' Clin Cancer Res, 13(7):2151-7.
Okudaira K et al., (2009), 'Blockade of B7-H1 or B7-DC Induces an Anti-Tumor Effect in a Mouse Pancreatic Cancer Model,' Int J Oncol, 35(4):741-9.
Parsa AT et al., (2007), 'Loss of Tumor Suppressor PTEN Function Increases B7-H1 Expression and Immunoresistance in Glioma,' Nat Med, 13(1):84-8.
Radhakrishnan S et al., (2003), 'Naturally Occurring Human IgM Antibody that Binds B7-DC and Potentiates T Cell Stimulation by Dendritic Cells,' J Immunol, 170(4):1830-8 (Retracted on Jun. 1, 2010).
Radhakrishnan S et al., (2004), 'Blockade of Allergic Airway Inflammation Following Systemic Treatment with a B7-Dendritic Cell (PD-L2) Cross-Linking Human Antibody,' J Immunol, 173(2):1360-5 (Retracted Jun. 1, 2010).
Radhakrishnan S et al., (2004), 'Immunotherapeutic Potential of B7-DC (PD-L2) Cross-Linking Antibody in Conferring Antitumor Immunity,' Cancer Res, 64(14):4965-72 (Retracted Nov. 15, 2010).
Radhakrishnan S et al., (2005), 'Dendritic Cells Activated by Cross-Linking B7-DC (PD-L2) Block Inflammatory Airway Disease,' J Allergy Clin Immunol, 116(3):668-74 (Retracted in 2010).
Schreiner B et al., (2004), 'Interferon-β enhances Monocyte and Dendritic Cell Expression of B7-H1 (PD-L1), a Strong Inhibitor of Autologous T-Cell Activation: Relevance for the Immune Modulatory Effect in Multiple Sclerosis,' J Neuroimmunol, 155(1-2):172-82.
Sierro SR et al., (2011), 'Combination of Lentivector Immunization and Low-Dose Chemotherapy or PD-1/PD-L1 Blocking Primes Self-Reactive T Cells and Induces Anti-Tumor Immunity,' Eur J Immunol, 41(8):2217-28.
Tseng SY et al., (2001), 'B7-DC, a New Dendritic Cell Molecule with Potent Costimulatory Properties for T Cells,' J Exp Med, 193(7):839-46.
Ueda H et al., (2003), 'Association of the T-Cell Regulatory Gene CTLA4 with Susceptibility to Autoimmune Disease,' Nature, 423(6939):506-11.
Wan B et al., (2006), 'Aberrant Regulation of Synovial T Cell Activation by Soluble Costimulatory Molecules in Rheumatoid Arthritis,' J Immunol, 177(12):8844-50.
Wells JA, (1996), 'Binding in the Growth Hormone Receptor Complex,' Proc Natl Acad Sci USA, 93(1):1-6.
Written Opinion of the International Searching Authority (Form ISA-237) for International application No. PCT/EP2012/004822 dated Mar. 1, 2013 (8 pages).
Yamazaki T et al., (2002), 'Expression of Programmed Death 1 Ligands by Murine T Cells and APC,' J Immunol, 169(10):5538-45.
Zhang L et al., (2009), 'PD-1/PDL1 Interactions Inhibit Antitumor Immune Responses in a Murine Acute Myeloid Leukemia Model,' Blood, 114(8):1545-52.
Zhong X et al., (2007), 'PD-L2 Expression Extends Beyond Dendritic Cells/Macrophages to B1 Cells Enriched for V(H)11/V(H)12 and Phosphatidylcholine Binding,' Eur J Immunol, 37(9):2405-10.
Abdiche et al (2016), "Assessing kinetic and epitopic diversity across orthogonal monoclonal antibody generation platforms," 8(2):264-277.
Boyd and Crowe, (2016) "Deep sequencing and human antibody repertoire analysis", Current Opinion in Immunology, 40:103-109.
Conroy et al. (2017), "Antibodies: From novel repertoires to defining and refining the structure of biologically important targets," Methods, 116:12-22.
Damschroder et al. (2004), "Analysis of human and primate CD2 molecules by protein sequence and epitope mapping with anti-human CD2 antibodies", Molecular Immunology, 41(10):985-1000.
Ferrara et al. (2015), "Recombinat renewable polyclonal antibodies", mAbs, 7(1):32-41.

(56) References Cited

OTHER PUBLICATIONS

Kahn et al, (2017), "Cross-neutralizing anti-HIV-1 human single chain variable fragments(scFvs) against CD4 binding site and N332 glycan identified from a recombinant phage library" Sci Rep. 7:1-12.

Konitzer et al. (2017), "Generation of a highly diverse panel of antagonistic chicken monoclonal antibodies against the GIP receptor," mAbs, 9(3):536-549.

Lee et al., (2016) "Molecular-level analysis of the serum antibody repertoire in young adults before and after seasonal influenza vaccination," Nature Medicine, 22(12): 1456-1464.

Mangsbo et al (2010), "Enhanced tumor eradication by combining CTLA-4 or PD-1 blockade with CpG therapy", 33(3):225-35.

Parola et al (2018) "Integrating high-throughput screening and sequencing for monoclonal antibody discovery and engineering," Immunology, 153(1):31-41.

Van Regenmortel (2018), "Development of a Preventive HIV Vaccine Requires Solving Inverse Problems Which Is Unattainable by Rational Vaccine Design,", 8(2009):1-11.

Sheehan and Marasco (2015) "Phage and Yeast Display," ASMscience.org/Microbiol Spectrum, 3(1): 1-17.

Zhou et al. (2015), "Structural Repertoire of HIV-1-Neutralizing Antibodies Targeting the CD4 Supersite in 14 Donors", Cell. 161(6):1280-92.

Lin et al., (2008), "The PD-1/PD-L1 complex resembles the antigen-binding Fv domains of antibodies and T cell receptors," Proc Natl Acad Sci U S A., 105(8):3011-3016.

Lee et al., "Molecular mechanism of PD-1/PD-L1 blockade via anti-PD-L1 antibodies atezolizumab and durvalumab," Scientific Reports, 7(1):5532; Jul. 17, 2017.

Simonyan et al., "Conformational Epitope Mapping by Cross-link Mass Spectrometry: Analysis of Ipilimumab, Nivolumab and Pembrolizumab," Nov. 15, 2017, retrieved from the Internet: URL: <https://covalx.com/pdf/CovalX-PEGSEU17Poster-XLMS_XRC_Comparison.pdf> (retrieved on Jun. 3, 2019).

Niman et al., "Generation of protein-reactive antibodies by short peptides is an event of high frequency: implications for the structural basis of immune recognition," Proc. Nat. Acad. Sci. USA, 80(16):4949-53; 1983.

U.S. Pat. No. 10,759,856, Anti-PD-L1 Antibodies and Uses Thereof, filed Sep. 1, 2020.

U.S. Pat. No. 10,487,147, Anti-PD-L1 Antibodies and Uses Thereof, filed Nov. 26, 2019.

U.S. Pat. No. 9,624,298, Anti-PD-L1 Antibodies and Uses Thereof, filed May 27, 2014.

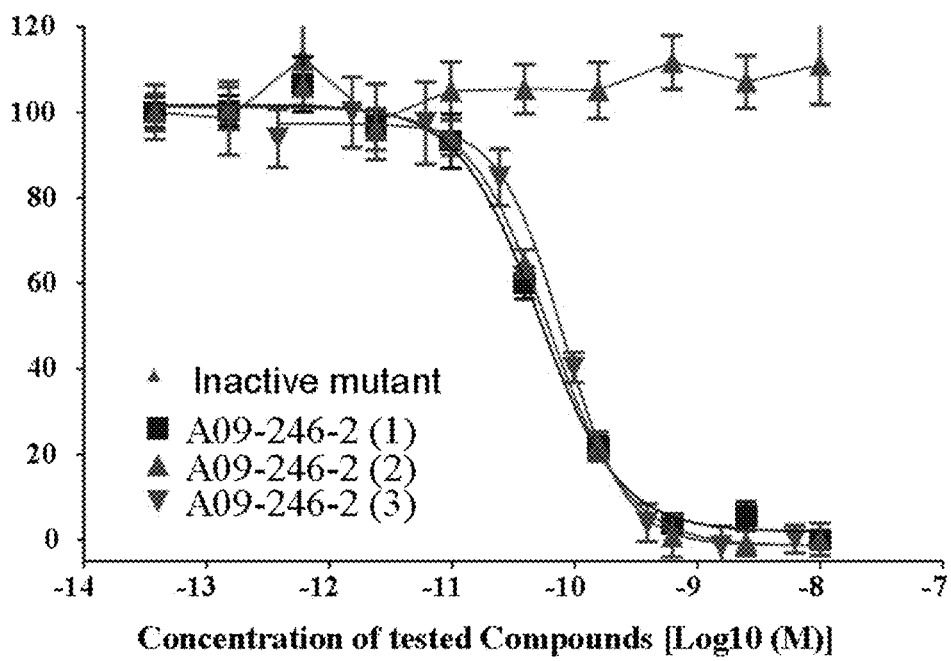

ANTI-PD-L1 ANTIBODIES AND USES THEREOF

CROSS-REFERENCE TO RELATED APPLICATIONS

This application is a continuation of U.S. patent application Ser. No. 15/454,939 filed Mar. 9, 2017, which is a divisional of U.S. patent application Ser. No. 14/360,775 filed May 27, 2014, which issued as U.S. Pat. No. 9,624,293, which is a national stage entry under 35 U.S.C. § 371 of International Patent Application No. PCT/EP2012/004822 filed Nov. 21, 2012, which claims priority to and the benefit of U.S. Provisional Patent Application No. 61/563,903 filed Nov. 28, 2011.

FIELD OF THE INVENTION

The present application relates to anti-PD-L1 antibodies or antigen binding fragments thereof, nucleic acid encoding the same, therapeutic compositions thereof, and their use to enhance T-cell function to upregulate cell-mediated immune responses and for the treatment of T cell dysfunctional disorders, such as tumor immunity, for the treatment of and cancer.

BACKGROUND OF THE INVENTION

Lymphocyte Development and Activation

The two major types of lymphocytes in humans are T (thymus-derived) and B (bone marrow derived. These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cells, on the other hand, develop from immature precursors that leave the marrow and travel through the bloodstream to the thymus, where they proliferate and differentiate into mature T lymphocytes.

Mature lymphocytes that emerge from the thymus or bone marrow are in a quiescent, or "resting" state, i.e., they are mitotically inactive. When dispersed into the bloodstream, these "naive" or "virgin" lymphocytes, travel into various secondary or peripheral lymphoid organs, such as the spleen, lymph nodes or tonsils. Most virgin lymphocytes have an inherently short life span and die without a few days after leaving the marrow or thymus. However, if such a cell receives signals that indicate the presence of an antigen, they may activate and undergo successive rounds of cell division. Some of the resulting progeny cells then revert to the resting state to become memory lymphocytes—B and T cells that are essentially primed for the next encounter with the stimulating allergen. The other progeny of activated virgin lymphocytes are effector cells, which survive for only a few days, but carry out specific defensive activities.

Lymphocyte activation refers to an ordered series of events through which a resting lymphocyte passes as it is stimulated to divide and produce progeny, some of which become effector cells. A full response includes both the induction of cell proliferation (mitogenesis) and the expression of immunologic functions. Lymphocytes become activated when specific ligands bind to receptors on their surfaces. The ligands are different for T cells and B cells, but the resulting intracellular physiological mechanisms are similar.

Some foreign antigens themselves can induce lymphocyte activation, especially large polymeric antigens that cross-link surface immunoglobulins on B-cells, or other glycoproteins on T-cells. However, most antigens are not polymeric and even direct binding to B-cells in large numbers fail to result in activation. These more common antigens activate B cells when they are co-stimulated with nearby activated helper T-lymphocytes. Such stimulation may occur from lymphokines secreted by the T-cell, but is transmitted most efficiently by direct contact of the B cell with T-cell surface proteins that interact with certain B-cell surface receptors to generate a secondary signal.

T-Cells

T lymphocytes do not express immunoglobulins, but, instead detect the presence of foreign substances by way of surface proteins called T-cell receptors (TCR). These receptors recognize antigens by either direct contact or through influencing the activity of other immune cells. Together with macrophages, T cells are the primary cell type involved in the cell-mediated immunity.

Unlike B-cells, T-cells can detect foreign substances only in specific contexts. In particular, T-lymphocytes will recognize a foreign protein only if it first cleaved into small peptides, which are then displayed on the surface of a second host cell, called an antigen-presenting cell (APC). Many types of host cells can present antigens under some conditions but certain types are more specifically adapted for this purpose and are particularly important in controlling T-cell activity, including macrophages and other B-cells. Antigen presentation depends in part on specific proteins, called major histocompatibility complex (MHC) proteins, on the surface of the presenting cells. Thus, to stimulate cell-mediated immunity, foreign peptides must be presented to T-cells in combination with MHC peptides, and this combination must be recognized by a T-cell receptor.

There are two significant T-cell subsets: cytotoxic T lymphocytes ($T_c$ cells or CTLs) and helper T cells (TH) cells, which can roughly be identified on the basis of cell surface expression of the marker CD8 and CD4. $T_c$ cells are important in viral defense, and can kill viruses directly by recognizing certain cell surface expressed viral peptides. TH cells promote proliferation, maturation and immunologic function of other cell types, e.g., lymphokine secretion to control activities of B cells, macrophages and cytotoxic T cells. Both virgin and memory T-lymphocytes ordinarily remain in the resting state, and in this state they do not exhibit significant helper or cytotoxic activity. When activated, these cells undergo several rounds of mitotic division to produce daughter cells. Some of these daughter cells return to the resting state as memory cells, but others become effector cells that actively express helper or cytotoxic activity. These daughter cells resemble their parents: CD4+ cells can only product CD4+ progeny, while CD8+ cells yield only CD8+ progeny. Effector T-cells express cell surface markers that are not expressed on resting T-cells, such as CD25, CD28, CD29, CD40L, transferrin receptors and class II MHC proteins. When the activating stimuli is withdrawn, cytotoxic or helper activity gradually subsides over a period of several days as the effector cells either die or revert to the resting state. Similar to B-cell activation, T-lymphocyte responses to most antigens also require two types of simultaneous stimuli. The first is the antigen, which if appropriately displayed by MHC proteins on an antigen-presenting cell, can be recognized and bound by T-cell receptors. While this antigen-MHC complex does send a signal to the cell interior, it is usually insufficient to result in T-cell activation. Full activation, such as occurs with helper T-cells, requires costimulation with other specific ligands called costimulators that are expressed on the surface of the antigen-presenting cell. Activation of a cytotoxic T cell, on the other hand, generally requires IL-2, a cytokine secreted by activated helper T cells.

PD-1 Pathway

An important negative co-stimulatory signal regulating T cell activation is provided by programmed death-1 receptor (PD-1)(CD279), and its ligand binding partners PD-L1 (B7-H1, CD274) and PD-L2 (B7-DC, CD273). The negative regulatory role of PD-1 was revealed by PD-1 knock outs (Pdcd1$^{-/-}$), which are prone to autoimmunity. Nishimura et al, Immunity JJ.: 141-51 (1999); Nishimura et al, Science 291: 319-22 (2001). PD-1 is related to CD28 and CTLA-4, but lacks the membrane proximal cysteine that allows homodimerization. The cytoplasmic domain of PD-1 contains an immunoreceptor tyorine-based inhibition motif (ITIM, V/lxYxxLN). PD-1 only binds to PD-L1 and PD-L2. Freeman et al, J. Exp. Med. 192: 1-9 (2000); Dong et al, Nature Med. 5: 1365-1369 (1999); Latchman et al, Nature Immunol 2: 261-268 (2001); Tseng et al, J. Exp. Med. 193: 839-846 (2001).

PD-1 can be expressed on T cells, B cells, natural killer T cells, activated monocytes and dendritic cells (DCs). PD-1 is expressed by activated, but not by unstimulated human CD4$^+$ and CD8$^+$ T cells, B cells and myeloid cells. This stands in contrast to the more restricted expression of CD28 and CTLA-4. Nishimura et al, Int. Immunol. 8: 773-80 (1996); Boettler et al, J. Virol. 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al, Cell. Immunol. 235: 109-16 (2005). With the exception of PD-1Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1Δex3 variants lacks a transmembrane domain, and resembles soluble CTLA-4, which plays an important role in autoimmunity. Ueda et al, Nature 423: 506-11 (2003). This variant is enriched in the synovial fluid and sera of patients with rheumatoid arthritis. Wan et al, J. Immunol. 177: 8844-50 (2006). The two PD-1 ligands differ in their expression patterns. PD-L1 is constitutively expressed on mouse T and B cells, CDs, macrophages, mesenchymal stem cells and bone marrow-derived mast cells. Yamazaki et al, J. Immunol. 169: 5538-45 (2002). PD-L1 is expressed on a wide range of nonhematopoietic cells (e.g., cornea, lung, vascular epithelium, liver nonpar enchymal cells, mesenchymal stem cells, pancreatic islets, placental synctiotrophoblasts, keratinocytes, etc.) [Keir et al, Annu. Rev. Immunol. 26: 677-704 (2008)], and is upregulated on a number of cell types after activation. Both type I and type II interferons IFN's) upregulate PD-L1. Eppihimer et al, Microcirculation 9: 133-45 (2002); Schreiner et al, J. Neuroimmunol 155: 172-82 (2004). PD-L1 expression in cell lines is decreased when MyD88, TRAF6 and MEK are inhibited. Liu et al, Blood HO: 296-304 (2007). JAK2 has also been implicated in PD-L1 induction. Lee et al, FEBS Lett. 580: 755-62 (2006); Liu et al, Blood HO: 296-304 (2007). Loss or inhibition of phosphatase and tensin homolog (PTEN), a cellular phosphatase that modified phosphatidylinosital 3-kinase (PI3K) and Akt signaling, increased post-transcriptional PD-L1 expression in cancers. Parsa et al, Nat. Med. 13: 84-88 (2007). PD-L2 expression is more restricted than PD-L1. PD-L2 is inducibly expressed on DCs, macrophages, and bone marrow-derived mast cells. PD-L2 is also expressed on about half to two-thirds of resting peritoneal BI cells, but not on conventional B2 B cells. Zhong et al, Eur. J. Immunol. 37: 2405-10 (2007). PD-L2+BI cells bind phosphatidylcholine and may be important for innate immune responses against bacterial antigens. Induction of PD-L2 by IFN-γ is partially dependent upon NF-KB. Liang et al, Eur. J. Immunol. 33_: 2706-16 (2003). PD-L2 can also be induced on monocytes and macrophages by GM-CF, IL-4 and IFN-γ. Yamazaki et al., J. Immunol. 169: 5538-45 (2002); Loke et al, PNAS 100:5336-41 (2003). PD-1 signaling typically has a greater effect on cytokine production than on cellular proliferation, with significant effects on IFN-γ, TNF-α and IL-2 production. PD-1 mediated inhibitory signaling also depends on the strength of the TCR signaling, with greater inhibition delivered at low levels of TCR stimulation. This reduction can be overcome by costimulation through CD28 [Freeman et al, J. Exp. Med. 192: 1027-34 (2000)] or the presence of IL-2 [Carter et al, Eur. J. Immunol. 32: 634-43 (2002)]. Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritric cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-α and IL-6, and stimulated T cell proliferation. Nguyen et al, J. Exp. Med. 196: 1393-98 (2002). Treatment of mice with this antibody also (1) enhanced resistance to transplated b16 melanoma and rapidly induced tumor-specific CTL. Radhakrishnan et al, J. Immunol. 170: 1830-38 (2003); Radhakrishnan et al, Cancer Res. 64: 4965-72 (2004); Heckman et al, Eur. J. Immunol. 37: 1827-35 (2007); (2) blocked development of airway inflammatory disease in a mouse model of allergic asthma. Radhakrishnan et al, J. Immunol. 173: 1360-65 (2004); Radhakrishnan et al, J. Allergy Clin. Immunol. UJy. 668-74 (2005).

Further evidence of reverse signaling into dendritic cells ("DCs") results from studies of bone marrow derived DCs cultured with soluble PD-1 (PD-1 EC domain fused to Ig constant region-"s-PD-1"). Kuipers et al, Eur. J. Immunol. 36: 2472-82 (2006). This sPD-1 inhibited DC activation and increased IL-10 production, in a manner reversible through administration of anti-PD-1. Additionally, several studies show a receptor for PD-L1 or PD-L2 that is independent of PD-1. B7.1 has already been identified as a binding partner for PD-1. Butte et al, Immunity 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T-cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

The direct interaction between B7.1 and PD-L1 suggests that the current understanding of costimulation is incomplete, and underscores the significance to the expression of these molecules on T cells. Studies of PD-L1$^{-/-}$ T cells indicate that PD-L1 on T cells can downregulate T cell cytokine production. Latchman et al, Proc. Natl. Acad. Sci. USA 101: 10691-96 (2004). Because both PD-L1 and B7.1 are expressed on T cells, B cells, DCs and macrophages, there is the potential for directional interactions between B7.1 and PD-L1 on these cells types. Additionally, PD-L1 on non-hematopoietic cells may interact with B7.1 as well as PD-1 on T cells, raising the question of whether PD-L1 is involved in their regulation. One possible explanation for the inhibitory effect of B7.1: PD-L1 interaction is that T cell PD-L1 may trap or segregate away APC B7.1 from interaction with CD28.

As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1: PD-L1 signaling, for example, antagonist anti-PD-1 and anti-PD-L2 antibodies.

In particular, the inhibition of PD-L1 signaling has been proposed as a means to enhance T cell immunity for the treatment of cancer (e.g., tumor immunity) and infection, including both acute and chronic (e.g., persistent) infection.

Inhibitors blocking the PD-L1: PD-1 interaction are known from, i.a., WO2001014557, WO2002086083, WO2007005874, WO2010036959, WO2010077634 and WO2011066389. However, as an optimal therapeutic directed to a target in this pathway has yet to be commercialized, a significant unmet medical need exists.

DESCRIPTION OF THE INVENTION

It is an objective of the present invention to provide for anti-PD-L1 antibodies, including nucleic acids encoding and compositions containing such antibodies, and for their use to enhance T-cell function to upregulate cell-mediated immune responses and for the treatment of T cell dysfunctional disorders, such as tumor immunity. Surprisingly, it was found that the anti-PD-L1 antibodies according to the present invention, which have antibody dependent cell-mediated cytotoxicity (ADCC) activity, directly act on PD-L1 bearing tumor cells by inducing their lysis without showing any significant toxicity. Moreover, the antibodies do not only block the interaction between human PD-L1 and human PD-1, but also the interactions between the respective mouse and cynomolgus monkey proteins.

In one embodiment, the invention provides for an isolated heavy chain variable region polypeptide comprising an HVR-H1, HVR-H2 and HVR-H3 sequence, wherein:
  (a) the HVR-H1 sequence is $X_1YX_2MX_3$ (SEQ ID NO:1);
  (b) the HVR-H2 sequence is SIYPSGGX$_4$TFYADX$_5$VKG (SEQ ID NO:2);
  (c) the HVR-H3 sequence is IKLGTVTTVX$_6$Y (SEQ ID NO:3);
  further wherein: $X_1$ is K, R, T, Q, G, A, W, M, I or S; $X_2$ is V, R, K, L, M or I; $X_3$ is H, T, N, Q, A, V, Y, W, F or M; $X_4$ is F or I; $X_5$ is S or T; $X_6$ is E or D.

In a preferred embodiment $X_1$ is M, I or S; $X_2$ is R, K, L, M or I; $X_3$ is F or M; $X_4$ is F or I; $X_5$ is S or T; $X_6$ is E or D.

In a more preferred embodiment is $X_1$ is M, I or S; $X_2$ is L, M or I; $X_3$ is F or M; $X_4$ is I; $X_5$ is S or T; $X_6$ is D.

In a even more preferred embodiment, $X_1$ is S; $X_2$ is I; $X_3$ is M; $X_4$ is I; $X_5$ is T; $X_6$ is D.

In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4).

In yet another aspect, the framework sequences are derived from human consensus framework sequences or human germline framework sequences.

In a still further aspect, at least one of the framework sequences is the following:

```
                                          (SEQ ID NO: 4)
HC-FR1 is     EVQLLESGGGLVQPGGSLRLSCAASGFTFS;

(SEQ ID NO: 5)
HC-FR2 is     WVRQAPGKGLEEVS;

(SEQ ID NO: 6)
HC-FR3 is     RFTISRDNSKNTLYLQMNSLRAEDTAVYYCAR;

(SEQ ID NO: 7)
HC-FR4 is     WGQGTLVTVSS.
```

In a still further aspect, the heavy chain polypeptide is further combined with a variable region light chain comprising an HVR-L1, HVR-L2 and HVR-L3, wherein:
  (a) the HVR-L1 sequence is TGTX$_7$X$_8$DVGX$_9$YNYVS (SEQ ID NO:8);
  (b) the HVR-L2 sequence is X$_{10}$VX$_{11}$X$_{12}$RPS (SEQ ID NO:9);
  (c) the HVR-L3 sequence is SSX$_{13}$TX$_{14}$X$_{15}$X$_{16}$X$_{17}$RV (SEQ ID NO:10);
  further wherein: $X_7$ is N or S; $X_8$ is T, R or S; $X_9$ is A or G; $X_{10}$ is E or D; $X_{11}$ is I, N or S; $X_{12}$ is D, H or N; $X_{13}$ is F or Y; $X_{14}$ is N or S; $X_{15}$ is R, T or S; $X_{16}$ is G or S; $X_{17}$ is I or T.

In a preferred embodiment, $X_7$ is N or S; $X_8$ is T, R or S; $X_9$ is A or G; $X_{10}$ is E or D; $X_{11}$ is N or S; $X_{12}$ is N; $X_{13}$ is F or Y; $X_{14}$ is S; $X_{15}$ is S; $X_{16}$ is G or S; $X_{17}$ is T.

In a even more preferred embodiment, $X_7$ is S; $X_8$ is S; $X_9$ is G; $X_{10}$ is D; $X_{11}$ is S; $X_{12}$ is N; $X_{13}$ is Y; $X_{14}$ is S; $X_{15}$ is S; $X_{16}$ is S; $X_{17}$ is T.

In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4).

In a still further aspect, the light chain framework sequences are derived from human consensus framework sequences or human germline framework sequences.

In a still further aspect, the light chain framework sequences are lambda light chain sequences.

In a still further aspect, at least one of the framework sequence is the following:

```
                                          (SEQ ID NO: 11)
LC-FR1 is     QSALTQPASVSGSPGQSITISC;

(SEQ ID NO: 12)
LC-FR2 is     WYQQHPGKAPKLMIY;
```

-continued

LC-FR3 is    GVSNRFSGSKSGNTASLTISGLQAEDEADYYC;    (SEQ ID NO: 13)

LC-FR4 is    FGTGTKVTVL.    (SEQ ID NO: 14)

In another embodiment, the invention provides an isolated anti-PD-L1 antibody or antigen binding fragment comprising a heavy chain and a light chain variable region sequence, wherein:
(a) the heavy chain comprises an HVR-H1, HVR-H2 and HVR-H3, wherein further: (i) the HVR-H1 sequence is $X_1YX_2MX_3$ (SEQ ID NO:1); (ii) the HVR-H2 sequence is SIYPSGGX$_4$TFYADX$_5$VKG (SEQ ID NO:2); (iii) the HVR-H3 sequence is IKLGTVTTVX$_6$Y, and (SEQ ID NO:3);
(b) the light chain comprises an HVR-L1, HVR-L2 and HVR-L3, wherein further: (iv) the HVR-L1 sequence is TGTX$_7$X$_8$DVGX$_9$YNYVS (SEQ ID NO:8); (v) the HVR-L2 sequence is X$_{10}$VX$_{11}$X$_{12}$RPS (SEQ ID NO:9); (vi) the HVR-L3 sequence is SSX$_{13}$TX$_{14}$X$_{15}$X$_{16}$X$_{17}$RV (SEQ ID NO:10); wherein: $X_1$ is K, R, T, Q, G, A, W, M, I or S; $X_2$ is V, R, K, L, M or I; $X_3$ is H, T, N, Q, A, V, Y, W, F or M; $X_4$ is F or I; $X_5$ is S or T; $X_6$ is E or D; $X_7$ is N or S; $X_8$ is T, R or S; $X_9$ is A or G; $X_{10}$ is E or D; $X_{11}$ is I, N or S; $X_{12}$ is D, H or N; $X_{13}$ is F or Y; $X_{14}$ is N or S; $X_{15}$ is R, T or S; $X_{16}$ is G or S; $X_{17}$ is I or T.

In a preferred embodiment, $X_1$ is M, I or S; $X_2$ is R, K, L, M or I; $X_3$ is F or M; $X_4$ is F or I; $X_5$ is S or T; $X_6$ is E or D; $X_7$ is N or S; $X_8$ is T, R or S; $X_9$ is A or G; $X_{10}$ is E or D; $X_{11}$ is N or S; $X_{12}$ is N; $X_{13}$ is F or Y; $X_{14}$ is S; $X_{15}$ is S; $X_{16}$ is G or S; $X_{17}$ is T.

In a more preferred embodiment, $X_1$ is M, I or S; $X_2$ is L, M or I; $X_3$ is F or M; $X_4$ is I; $X_5$ is S or T; $X_6$ is D; $X_7$ is N or S; $X_8$ is T, R or S; $X_9$ is A or G; $X_{10}$ is E or D; $X_{11}$ is N or S; $X_{12}$ is N; $X_{13}$ is F or Y; $X_{14}$ is S; $X_{15}$ is S; $X_{16}$ is G or S; $X_{17}$ is T.

In a even more preferred embodiment, $X_1$ is S; $X_2$ is I; $X_3$ is M; $X_4$ is I; $X_5$ is T; $X_6$ is D; $X_7$ is S; $X_8$ is S; $X_9$ is G; $X_{10}$ is D; $X_{11}$ is S; $X_{12}$ is N; $X_{13}$ is Y; $X_{14}$ is S; $X_1$ is S; $X_1$ is S; $X_{17}$ is T.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences or human germline sequences.

In a still further aspect, one or more of the heavy chain framework sequences is the following:

HC-FR1 is    EVQLLESGGGLVQPGGSLRLSCAASGFTFS;    (SEQ ID NO: 4)

HC-FR2 is    WVRQAPGKGLEWVS;    (SEQ ID NO: 5)

HC-FR3 is    RFTISRDNSKNTLYLQMNSLRAEDTAVYYCAR;    (SEQ ID NO: 6)

HC-FR4 is    WGQGTLVTVSS.    (SEQ ID NO: 7)

In a still further aspect, the light chain framework sequences are lambda light chain sequences.

In a still further aspect, one or more of the light chain framework sequences is the following:

LC-FR1 is    QSALTQPASVSGSPGQSITISC;    (SEQ ID NO: 11)

LC-FR2 is    WYQQHPGKAPKLMIY;    (SEQ ID NO: 12)

LC-FR3 is    GVSNRFSGSKSGNTASLTISGLQAEDEADYYC;    (SEQ ID NO: 13)

LC-FR4 is    FGTGTKVTVL.    (SEQ ID NO: 14)

In a still further aspect, the heavy chain variable region polypeptide, antibody or antibody fragment further comprises at least a $C_H1$ domain.

In a more specific aspect, the heavy chain variable region polypeptide, antibody or antibody fragment further comprises a $C_H1$, a $C_H^2$ and a $C_H^3$ domain.

In a still further aspect, the variable region light chain, antibody or antibody fragment further comprises a $C_L$ domain.

In a still further aspect, the antibody further comprises a $C_H^1$, a $C_H^2$, a $C_H^3$ and a $C_L$ domain.

In a still further specific aspect, the antibody further comprises a human or murine constant region.

In a still further aspect, the human constant region is selected from the group consisting of IgG1, IgG2, IgG2, IgG3, IgG4.

In a still further specific aspect, the human or murine constant region is IgG1.

In yet another embodiment, the invention provides for an anti-PD-L1 antibody comprising a heavy chain and a light chain variable region sequence, wherein:
(a) the heavy chain comprises an HVR-H1, HVR-H2 and an HVR-H3, having at least 80% overall sequence identity to SYIMM (SEQ ID NO:15), SIYPSGGITFYADTVKG (SEQ ID NO:16) and IKLGTVTTVDY (SEQ ID NO:17), respectively, and
(b) the light chain comprises an HVR-L1, HVR-L2 and an HVR-L3, having at least 80% overall sequence identity to TGTSSDVGGYNYVS (SEQ ID NO:18), DVSNRPS (SEQ ID NO:19) and SSYTSSSTRV (SEQ ID NO:20), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99% or 100%.

In yet another embodiment, the invention provides for an anti-PD-L1 antibody comprising a heavy chain and a light chain variable region sequence, wherein:
(a) the heavy chain comprises an HVR-H1, HVR-H2 and an HVR-H3, having at least 80% overall sequence identity to MYMMM (SEQ ID NO:21), SIYPSG-GITFYADSVKG (SEQ ID NO:22) and IKLGTVTTVDY (SEQ ID NO:17), respectively, and
(b) the light chain comprises an HVR-L1, HVR-L2 and an HVR-L3, having at least 80% overall sequence identity to TGTSSDVGAYNYVS (SEQ ID NO:23), DVSNRPS (SEQ ID NO:19) and SSYTSSSTRV (SEQ ID NO:20), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99% or 100%.

In a still further aspect, in the antibody or antibody fragment according to the invention, as compared to the sequences of HVR-H1 (SEQ ID NO:15), HVR-H2 (SEQ ID NO:16) and HVR-H3 (SEQ ID NO:17), at least those amino acids remain unchanged that are highlighted by underlining as follows:

(a) in HVR-H1    SYIMM,              (SEQ ID NO: 15)
(b) in HVR-H2    SIYPSGGITFYADTVKG,  (SEQ ID NO: 16)
(c) in HVR-H3    IKLGTVTTVDY;        (SEQ ID NO: 17)

and further wherein, as compared to the sequences of HVR-L1 (SEQ ID NO:18), HVR-L2 (SEQ ID NO:19) and HVR-L3 (SEQ ID NO:20) at least those amino acids remain unchanged that are highlighted by underlining as follows:

(a) HVR-L1    TGTSSDVGGYNYVS    (SEQ ID NO: 18)
(b) HVR-L2    DVSNRPS           (SEQ ID NO: 19)
(c) HVR-L3    SSYTSSSTRV.       (SEQ ID NO: 20)

In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4).

In yet another aspect, the framework sequences are derived from human germline sequences.

In a still further aspect, one or more of the heavy chain framework sequences is the following:

(SEQ ID NO: 4)
HC-FR1 is    EVQLLESGGGLVQPGGSLRLSCAASGFTFS;

(SEQ ID NO: 5)
HC-FR2 is    WVRQAPGKGLEEVS;

(SEQ ID NO: 6)
HC-FR3 is    RFTISRDNSKNTLYLQMNSLRAEDTAVYYCAR;

(SEQ ID NO: 7)
HC-FR4 is    WGQGTLVTVSS.

In a still further aspect, the light chain framework sequences are derived from a lambda light chain sequence.

In a still further aspect, one or more of the light chain framework sequences is the following:

(SEQ ID NO: 11)
LC-FR1 is    QSALTQPASVSGSPGQSITISC;

(SEQ ID NO: 12)
LC-FR2 is    WYQQHPGKAPKLMIY;

(SEQ ID NO: 13)
LC-FR3 is    GVSNRFSGSKSGNTASLTISGLQAEDEADYYC;

(SEQ ID NO: 14)
LC-FR4 is    FGTGTKVTVL.

In a still further specific aspect, the antibody further comprises a human or murine constant region.

In a still further aspect, the human constant region is selected from the group consisting of IgG1, IgG2, IgG2, IgG3, IgG4.

In a still further embodiment, the invention provides for an isolated anti-PD-L1 antibody comprising a heavy chain and a light chain variable region sequence, wherein:
(a) the heavy chain sequence has at least 85% sequence identity to the heavy chain sequence:

(SEQ ID NO: 24)
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSS, (b) the light chain sequence has at least 85% sequence identity to the light chain sequence:

(SEQ ID NO: 25)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL.

In a specific aspect, the sequence identity is 86%, 87%, 88%, 89%, 90%, 91%, 92%, 93%, 94%, 95%, 96%, 97%, 98%, 99% or 100%.

In a still further embodiment, the invention provides for an isolated anti-PD-L1 antibody comprising a heavy chain and a light chain variable region sequence, wherein:
(a) the heavy chain sequence has at least 85% sequence identity to the heavy chain sequence:

(SEQ ID NO: 26)
EVQLLESGGGLVQPGGSLRLSCAASGFTFSMYMMMWVRQAPGKGLEWVSS

IYPSGGITFYADSVKGRFTISRDNSKNTLYLQMNSLRAEDTAIYYCARIK

LGTVTTVDYWGQGTLVTVSS, and
(b) the light chain sequence has at least 85% sequence identity to the light chain sequence:

(SEQ ID NO: 27)
QSALTQPASVSGSPGQSITISCTGTSSDVGAYNYVSWYQQHPGKAPKLMI

YDVSNRPSGVSNRFSGSKSGNTASLTISGLQAEDEADYYCSSYTSSSTRV

FGTGTKVTVL.

In a specific aspect, the sequence identity is 86%, 87%, 88%, 89%, 90%, 91%, 92%, 93%, 94%, 95%, 96%, 97%, 98%, 99% or 100%.

In another embodiment the antibody binds to human, mouse or cynomolgus monkey PD-L1. In a specific aspect the antibody is capable of blocking the interaction between human, mouse or cynomolgus monkey PD-L1 and the respective human, mouse or cynomolgus monkey PD-1 receptors.

In another embodiment, the antibody binds to human PD-L1 with a $K_D$ of $5 \times 10^{-9}$ M or less, preferably with a $K_D$ of $2 \times 10^{-9}$ M or less, and even more preferred with a $K_D$ of $1 \times 10^{-9}$ M or less.

In yet another embodiment the invention concerns an isolated anti-PD-L1 antibody or antigen binding fragment thereof which binds to a functional epitope comprising residues Y56 and D61 of human PD-L1 (SEQ ID NO:28).

In a specific aspect, the functional epitope further comprises E58, E60, Q66, R113 and M115 of human PD-L1 (SEQ ID NO:28).

In a more specific aspect, the antibody binds to a conformational epitope, comprising residues 54-66 and 112-122 of human PD-L1 (SEQ ID NO:28).

In a further embodiment, the invention is related to an anti-PD-L1 antibody, or antigen binding fragment thereof, which cross-competes for binding to PD-L1 with an antibody according to the invention as described herein.

In a still further embodiment, the invention provides for compositions comprising any of the above described anti-PD-L1 antibodies in combination with at least one pharmaceutically acceptable carrier.

In a still further embodiment, the invention provides for an isolated nucleic acid encoding a polypeptide, or light chain or a heavy chain variable region sequence of an anti-PD-L1 antibody, or antigen binding fragment thereof, as described herein.

In a still further embodiment, the invention provides for an isolated nucleic acid encoding a light chain or a heavy chain variable region sequence of an anti-PD-L1 antibody, wherein:
 (a) the heavy chain comprises an HVR-H1, HVR-H2 and an HVR-H3 sequence having at least 80% sequence identity to SYIMM (SEQ ID NO:15), SIYPSGGITFY-ADTVKG (SEQ ID NO:16) and IKLGTVTTVDY (SEQ ID NO:17), respectively, or
 (b) the light chain comprises an HVR-L1, HVR-L2 and an HVR-L3 sequence having at least 80% sequence identity to TGTSSDVGGYNYVS (SEQ ID NO:18), DVSNRPS (SEQ ID NO:19) and SSYTSSSTRV (SEQ ID NO:20), respectively.

In a specific aspect, the sequence identity is 81%, 82%, 83%, 84%, 85%, 86%, 87%, 88%, 89%, 90%, 91%, 92%, 93%, 94%, 95%, 96%, 97%, 98%, 99% or 100%.

In a further aspect the nucleic acid is SEQ ID NO:30 for the heavy chain, and SEQ ID NO:31 for the light chain.

In another aspect, the nucleic acid further comprises a vector suitable for expression of the nucleic acid encoding any of the previously described anti-PD-L1 antibodies.

In a still further specific aspect, the vector further comprises a host cell suitable for expression of the nucleic acid.

In a still further specific aspect, the host cell is a eukaryotic cell or a prokaryotic cell.

In a still further specific aspect, the eukaryotic cell is a mammalian cell, such as Chinese Hamster Ovary (CHO).

In a still further embodiment, the invention provides for a process of making an anti-PD-L1 antibody or antigen binding fragment thereof, comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

In a still further embodiment, the invention provides a kit of parts comprising a container enclosing a therapeutically effective amount of a composition disclosed herein and a package insert indicating use for the treatment of a T-cell dysfunctional disorder.

In a still further embodiment, the invention provides for a kit of parts comprising any of the above described anti-PD-L1 compositions in combination with at least one further therapeutic agent or vaccine, such as a chemotherapeutic agent.

In one aspect, the at least one chemotherapeutic agent is gemcitabine, cyclophosphamide, fluorouracil or oxaliplatin.

In another aspect, the vaccine is Stimuvax.

In a still further embodiment, the invention provides for a method of enhancing T-cell function comprising administering an effective amount of any of the above described anti-PD-L1 antibodies or compositions.

In one aspect, the anti-PD-L1 antibody or composition renders dysfunctional T-cells non-dysfunctional.

In another aspect, the antibody or composition treats of prevents a symptom of persistent infection, such as viral infection, e.g. by human immunodeficiency virus (HIV), herpes virus, Eppstein-Barr virus or human papilloma virus.

In a still further embodiment, the invention provides for a method of treating a T-cell dysfunctional disorder comprising administering a therapeutically effective amount of any of the above described anti-PD-L1 antibodies or compositions.

In one specific aspect, the T-cell dysfunctional disorder is tumor immunity.

In a still further aspect, the method further comprises treatment with a vaccine.

In a still further aspect, the PD-L1 antibody or composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

In a still further specific aspect, the tumor immunity results from a cancer selected from the group consisting of: breast, lung, colon, ovarian, melanoma, bladder, kidney, liver, salivary, stomach, gliomas, thyroid, thymic, epithelial, head and neck cancers, gastric, and pancreatic cancer.

Another aspect of the invention relates to the use of antibody dependent cell-mediated cytotoxicity (ADCC) of an anti-PD-L1 antibody disclosed herein or composition in the treatment of cancer.

Therefore, the invention pertains to method of treating cancer comprising administering to a subject in need thereof an effective amount of an anti-PD-L1 antibody which induces antibody dependent cell-mediated cytotoxicity (ADCC).

In a preferred embodiment the constant region of the anti-PD-L1 antibody is IgG1.

In another preferred embodiment the cancer is selected from the group consisting of: breast, lung, colon, ovarian, melanoma, bladder, kidney, liver, salivary, stomach, gliomas, thyroid, thymic, epithelial, head and neck cancers, gastric and pancreatic cancer.

Equivalent to the above mentioned methods of enhancing T-cell function, treating a T-cell dysfunctional disorder, or treating cancer, the invention relates likewise to the use of an anti-PD-L1 antibody or composition as described above and below for the manufacture of a medicament for enhancing T-cell function, treating a T-cell dysfunctional disorder or treating cancer; or to an anti-PD-L1 antibody or composition for use in the enhancement of T-cell function, or treatment of a T-cell dysfunctional disorder or cancer.

In yet a further embodiment, the invention is directed to engineered antibodies, or engineered antibody fragments, which are fused directly or via a linker molecule to therapeutic agents, such as cytokines (e.g. IL-2, IL-12, TNFa, IFNa, IFNb), or growth factors; which engineered antibodies or engineered antibody fragments may also be used in tumor therapy and immune system related diseases. Antibody fusion proteins, especially immunocytokines, are well known in the art. The fusion partner can be bound to the N-terminus of the antibody or antibody fragment or, preferably, to its C-terminus.

Definitions

"Dysfunction" in the context of immune dysfunction, refers to a state of immune reduced responsiveness to antigenic stimulation. The term includes the common elements of both exhaustion and/or anergy in which antigen recognition may occur, but the ensuing immune response is ineffective to control infection or tumor growth.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8$^+$ T-cells, increased proliferation, increased antigen responsiveness (e.g., viral or pathogen clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

The term "vaccine" as used herein includes any nonpathogenic immunogen that, when inoculated into a host, induces protective immunity against a specific pathogen. Vaccines can take many forms. Vaccines can be whole organisms that share important antigens with the pathogen, but are not pathogenic themselves (e.g., cowpox). Vaccines can also be prepared from killed (e.g., Salk polio vaccine) or attenuated (lost ability to produce disease—e.g., Sabin polio vaccine). Vaccines can also be prepared from purified macromolecules isolated from the pathogenic organism. For example, toxoid vaccines (e.g., tetanus and diphtheria) containing the inactive form of soluble bacterial toxin—resulting in the production of anti-toxin antibodies, but not immunity to the intact bacteria. Subunit vaccines (e.g., Hepatitis B) contain only a single immunogenic protein isolated from the pathogen of interest. Hapten conjugate vaccines attaches certain carbohydrate or polypeptide epitopes isolated from the pathogen of interest to immunogenic carriers, such as tetanus toxoid. These strategies essentially use the epitopes as haptens to induce antibody production, which then recognize the same epitope in the native pathogen. However, to be maximally effective, such vaccines must incorporate both B- and T-cell epitopes, and the T-cell epitopes must be chosen to ensure that they can be recognized, presented and responded to by the immune systems of the host individuals. DNA vaccines exploit the ability of host cells to take up and express DNA encoding pathogenic proteins that is injected intramuscularly. Host responses to immunogens can be enhanced if administered as a mixture with adjuvants. Immune adjuvants function in one or more of the following ways: (1) prolonging retention of the immunogen, (2) increased effective size of the immunogen (and hence promoting phagocytosis and presentation to macrophages), (3) stimulating the influx of macrophage or other immune cells to the injection site, or (4) promoting local cytokine production and other immunologic activities. Example adjuvants include: complete Freund's adjuvant (CFA), aluminum salts, and mycobacterial derived proteins such as muramyl di- or tri-peptides.

The term "antibody" includes monoclonal antibodies (including full length antibodies which have an immunoglobulin Fc region), antibody compositions with polyepitopic specificity, multispecific antibodies {e.g., bispecific antibodies, diabodies, and single-chain molecules, as well as antibody fragments (e.g., Fab, F(ab')2, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgK1.

An "isolated" antibody is one that has been identified, separated and/or recovered from a component of its production environment (E.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight, (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al, Sequences of Immunological Interest, Fifth Edition, National Institute of Health, Bethesda, MD (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256:495-97 (1975); Hongo et al, Hybridoma, 14 (3): 253-260 (1995), Harlow et al, Antibodies: A Laboratory Manual, (Cold Spring Harbor Laboratory Press, $2^{nd}$ ed. 1988); Hammerling et al, in: Monoclonal Antibodies and T-Cell Hybridomas 563-681 (Elsevier, N. Y., 1981)), recombinant DNA methods (see, e.g., U.S. Pat. No. 4,816,567), phage-display technologies (see, e.g., Clackson et al, Nature, 352: 624-628 (1991); Marks et al, J. Mol Biol. 222: 581-597 (1992); Sidhu et al, J. Mol Biol. 338(2): 299-310 (2004); Lee et al, J. Mol Biol. 340(5): 1073-1093 (2004); Fellouse, Proc. Natl. Acad. ScL USA 101(34): 12467-12472 (2004); and Lee et al, J. Immunol. Methods 284(1-2): 119-132 (2004), and technologies for producing human or humanlike antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al, Proc. Natl. Acad. ScL USA 90: 2551 (1993); Jakobovits et al, Nature 362: 255-258 (1993); Bruggemann et al, Year in Immunol. 7:33 (1993); U.S. Pat. Nos. 5,545,807; 5,545,806; 5,569,825; 5,625,126; 5,633,425; and 5,661,016; Marks et al, Bio/Technology 10: 779-783 (1992); Lonberg et al, Nature 368: 856-859 (1994); Morrison, Nature 368: 812-813 (1994); Fishwild et al, Nature Biotechnol 14: 845-851 (1996); Neuberger, Nature Biotechnol. 14: 826 (1996); and Lonberg and Huszar, Intern. Rev. Immunol. 13: 65-93 (1995).

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al, Protein Eng. 8HO): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (V$_H$), and the first constant domain of one heavy chain (C$_H$1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and-binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site. "Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994). "Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al, Proc. Natl. Acad. ScL USA 90: 6444-6448 (1993).

The term "nanobodies" refers to single-domain antibodies which are antibody fragments consisting of a single monomeric variable antibody domain. Like a whole antibody, they are able to bind selectively to a specific antigen. With a molecular weight of only 12-15 kDa, single-domain antibodies are much smaller than common antibodies (150-160 kDa). The first single-domain antibodies were engineered from heavy-chain antibodies found in camelids. Gibbs, W. Wayt (August 2005). "Nanobodies". Scientific American Magazine.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. ScL USA, 81:6851-6855 (1984)). As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al, Nature 321:522-525 (1986); Riechmann et al, Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982, 321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol, 227: 381 (1991); Marks et al, J. Mol. Biol, 222:581 (1991). Also available for the preparation of human monoclonal antibodies are methods described in Cole et al, Monoclonal Antibodies and Cancer Therapy, Alan R. Liss, p. 77 (1985); Boerner et al, J. Immunol, 147(1):86-95 (1991). See also van Dijk and van de Winkel, Curr. Opin. Pharmacol, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al, Immunity 13:37-45 (2000); Johnson and Wu, in Methods in Molecular Biology 248:1-25 (Lo, ed., Human Press, Totowa, NJ, 2003). Indeed, naturally occurring camelid antibodies consisting of a heavy chain only are functional and stable in the absence of light chain. See, e.g., Hamers-Casterman et al., Nature 363:446-448 (1993); Sheriff et al, Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed.

Public Health Service, National Institutes of Health, Bethesda, MD (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software.

The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5$^{th}$ Ed. Public Health Service, National Institutes of Health, Bethesda, MD (1991). Examples include for the VL, the subgroup may be subgroup kappa I, kappa II, kappa Ill or kappa IV as in Kabat et al, supra. Additionally, for the VH, the subgroup may be subgroup I, subgroup II, or subgroup Ill as in Kabat et al., supra.

Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al, Bio/Technology 10:779-783 (1992) describes affinity maturation by VH- and VL-domain shuffling. Random mutagenesis of HVR and/or framework residues is described by, for example: Barbas et al. Proc Nat. Acad. ScL USA 91:3809-3813 (1994); Schier et al. Gene 169:147-155 (1995); YdXon et al. J. Immunol. 155:1994-2004 (1995); Jackson et al, J. Immunol. 154(7):3310-9 (1995); and Hawkins et al, J. Mol. Biol. 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of $<1\times10^{-6}$ M, $<1\times10^{-7}$ M, $<1\times10^{-8}$ M, $<1\times10^{-9}$ M, or $<1\times10^{-10}$ M. In certain embodiments, an antibody specifically binds to an epitope on a protein that is conserved among the protein from different species. In another embodiment, specific binding can include, but does not require exclusive binding.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al, PNAS USA 95:652-656 (1998). Unless indicated otherwise herein, the numbering of the residues in an immunoglobulin heavy chain is that of the EU index as in Kabat et al, supra. The "EU index as in Kabat" refers to the residue numbering of the human IgG1 EU antibody. In many cancers the tumor cells express high levels of PD-L1 on their surface. Upon binding to PD-L1 on tumor cells and binding with their fragment crystalline (Fc) part to Fc-gamma receptors (FCGR) on leukocytes, anti-PD-L1 antibodies with ADCC potential can trigger ADCC which may lead to the death of these tumor cells.

The term "c region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4. "c receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see M. Daeron, Annu. Rev. Immunol. 15:203-234 (1997). FcRs are reviewed in Ravetch and Kinet, Annu. Rev. Immunol. 9: 457-92 (1991); Capel et al, Immunomethods 4: 25-34 (1994); and de Haas et al, J. Lab. Clin. Med. 126: 330-41 (1995). Other FcRs, including those to be identified in the future, are encompassed by the term "FcR" herein.

The term "c receptor" or "FcR" also includes the neonatal receptor, FcRn, which is responsible for the transfer of maternal IgGs to the fetus. Guyer et al, J. Immunol. 117: 587 (1976) and Kim et al., J. Immunol. 24: 249 (1994). Methods of measuring binding to FcRn are known (see, e.g., Ghetie and Ward, Immunol. Today 18: (12): 592-8 (1997); Ghetie et al, Nature Biotechnology 15 (7): 637-40 (1997); Hinton et al, J. Biol. Chem. TJI (8): 6213-6 (2004); WO 2004/92219 (Hinton et al). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al, J. Biol. Chem. 9(2): 6591-6604 (2001).

"Effector cells" are leukocytes which express one or more FcRs and perform effector functions. In one aspect, the effector cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source, e.g., blood. Effector cells generally are lymphocytes associated with the effector phase, and function to produce cytokines (helper T cells), killing cells in infected with pathogens (cytotoxic T cells) or secreting antibodies (differentiated B cells).

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., antibody Fab fragment and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The "$K_D$" or "$K_D$ value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al, (1999) J. Mol Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al, (1997) Cancer Res. 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (Micro Scint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the $K_D$ is measured by using surface-plasmon resonance assays using a BIACORE®-2000 or a BIACORE®-3000 instrument (BIAcore, Inc., Piscataway, NJ) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µL/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al, J. Mol. Biol. 293:865-881 (1999). If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate" "rate of association" "association rate" or "$k_{on}$" according to this invention can also be determined as described above using a BIACORE©-2000 or a BIACORE-3000 system (BIAcore, Inc., Piscataway, NJ) at 25° C. with immobilized antigen CM5 chips at about 10 response units (RU). Briefly, carboxymethylated dextran biosensor ships (CM5, BIAcore Inc.) are activated with N-ethyl-N'-(3-dimethylamino propyl)-carbodiimide hydrochloride (ECD) and N-hydroxysuccinimide (NHS) according to the supplier's instructions. Antigen is diluted with 10 mM sodium acetate, ph 4.8, into 5 mg/ml (~0.2 mM) before injection at a flow rate of 5 ml/min. to achieve approximately 10 response units (RU) of coupled protein. Following the injection of antigen, IM ethanolamine is added to block unreacted groups. For kinetics measurements, two-fold serial dilutions of Fab (0.78 nM to 500 nM) are injected in PBS with 0.05% Tween 20 (PBST) at 25° C. at a flow rate of approximatly 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant ($K_D$) was calculated as the ratio $k_{off}/k_{on}$. See, e.g., Chen, Y., et al, (1999) J. Mol Biol 293:865-881. However, if the on-rate exceeds $10^6$ $M^{-1}s^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (Thermo Sp ectronic) with a stirred cuvette.

The term "functional epitope" as used herein refers to amino acid residues of an antigen that contribute energetically to the binding of an antibody, i.e. forming an "energetic epitope". Mutation of any one of the energetically contributing residues of the antigen to alanine will disrupt the binding of the antibody such that the relative $K_D$ ratio ($K_D$ mutant PD-L1/$K_D$ wild type PD-L1) of the antibody will be greater than 4 (see Example 3.x(b)).

The term "conformational epitope" as used herein refers to amino acid residues of the PD-L1 antigen that come together on the surface when the polypeptide chain folds to form the native protein, and show a significantly reduced rate of HD exchange due to Fab binding, as described in the experimental section. The conformation epitope contains, but is not limited to, the functional epitope.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_D$ values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values {e.g., $K_D$ values). The difference between said two values is, for example, less than about 50%, less than about 40%, less than about 30%, less than about 20%, and/or less than about 10% as a function of the reference/comparator value.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2 or ALIGN software. Those skilled in the art can determine appropriate parameters for measuring alignment, including any algorithms needed to achieve maximal alignment over the full length of the sequences being compared.

A "blocking" antibody or an "antagonist" antibody is one that inhibits or reduces a biological activity of the antigen it binds to. In some embodiments, blocking antibodies or antagonist antibodies substantially or completely inhibit the biological activity of the antigen. The anti-PD-1 antibodies of the invention block the interaction between PD-L1 and its receptor PD-1, and thus the signaling through PD-1 so as to restore a functional response by T-cells from a dysfunctional state to antigen stimulation. An "agonist" or activating antibody is one that enhances or initiates signaling by the antigen to which it binds. In some embodiments, agonist antibodies cause or activate signaling without the presence of the natural ligand.

The terms "cross-compete", "cross-competition", "cross-block", "cross-blocked" and "cross-blocking" are used interchangeably herein to mean the ability of an antibody or fragment thereof to interfere with the binding directly or indirectly through allosteric modulation of the anti-PD-L1 antibodies of the invention to the target human PD-L1. The extent to which an antibody or fragment thereof is able to interfere with the binding of another to the target, and therefore whether it can be said to cross-block or cross-compete according to the invention, can be determined using competition binding assays. One particularly suitable quantitative cross-competition assay uses a FACS- or an AlphaScreen-based approach to measure competition between the labelled (e.g. His tagged, biotinylated or radioactive labelled) an antibody or fragment thereof and the other an antibody or fragment thereof in terms of their binding to the target. In the Experimental Section a suitable assay is described for determining whether a binding molecule cross-competes or is capable of cross-competing with an antibody or fragment thereof. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% to 100%.

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional A "stable" formulation is one in which the protein therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, New York, Pubs. (1991) and Jones, A. Adv. Drug Delivery Rev. 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, in certain embodiments of the invention, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer. "Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfuric, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-I-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine. Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and w-cresol. The most preferred preservative herein is benzyl alcohol.

"Treatment" refers to clinical intervention designed to alter the natural course of the individual or cell being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis. In some embodiments, antibodies of the invention are used to delay development of a disease or disorder. A subject is successfully "treated", for example, using the apoptotic anti-PD-L1 antibodies of the invention if one or more symptoms associated with a T-cell dysfunctional disorder is mitigated.

An "effective amount" refers to at least an amount effective, at dosages and for periods of time necessary, to achieve the desired or indicated effect, including a therapeutic or prophylactic result. For example, an effective amount of the anti-PD-L1 antibodies of the present invention is at least the minimum concentration that results in inhibition of signaling from PD-L1, either through PD-1 on T-cells or B7.1 on other APCs or both.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. For example, a therapeutically effective amount of the anti-PD-L1 antibodies of the present invention is at least the minimum concentration that results in inhibition of at least one symptom of a T cell dysfunctional disorder.

A "prophylactically effective amount" refers to an amount effective, at the dosages and for periods of time necessary, to achieve the desired prophylactic result. For example, a prophylactically effective amount of the anti-PD-L1 antibodies of the present invention is at least the minimum concentration that prevents or attenuates the development of at least one symptom of a T cell dysfunctional disorder.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "about" as used herein refers to the usual error range for the respective value readily known to the skilled person in this technical field.

An "autoimmune disorder" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Preferred such diseases include autoimmune rheumatologic disorders (such as, for example, RA, Sjogren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases {e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjogren's syndrome, Graves' disease, IDDM, pernicious anemia, thyroiditis, and glomerulonephritis.

The term "cytotoxic agent" as used herein refers to a substance that inhibits or prevents the function of cells and/or causes destruction of cells. The term includes radioactive isotopes (e.g. $At^{211}$, $I^{131}$, $I^{125}Y^{90}$, $Re^{186}$, $Re^{188}$, $Sm^{153}$, $Bi^{212}$, $P^{32}$ and radioactive isotopes of Lu), and toxins such as small-molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol); beta-lapachone; lapachol; colchicines; betulinic acid; a camptothecin (including the synthetic analogue topotecan (CPT-11 (irinotecan), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Nicolaou et ah, Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HCl liposome injection and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine, tegafur, capecitabine, an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; etoposide (VP-16); ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin combined with 5-FU and leucovovin.

Other therapeutic agents that may be used in combination with the anti-PD-L1 antibodies of the invention are bisphosphonates such as clodronate, NE-58095, zoledronic acid/zoledronate, alendronate, pamidronate, tiludronate, or risedronate; as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as Stimuvax vaccine, Theratope vaccine and gene therapy vaccines, for example, Allovectin vaccine, Leuvectin vaccine, and Vaxid vaccine; topoisomerase 1 inhibitor; an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH; lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

"Stimuvax" is a BLP25 liposome cancer vaccine designed to induce an immune response to cancer cells that express MUC1, a protein antigen widely expressed on common cancers. MUC1 is over expressed on many cancers such as lung cancer, breast cancer, prostate cancer and colorectal cancer. Stimuvax is thought to work by stimulating the body's immune system to identify and destroy cancer cells expressing MUC1.

BRIEF DESCRIPTION OF THE FIGURES

FIG. 1 shows that A09-246-2 efficiently blocks $^{125}$I-PD-L1 binding to immobilized PD-1-Fc. Inactive mutant: Mutant VL-A31G, D52E, R99Y of A09-188-1. A09-246-2 (1): Expressed in HEK 293 cells. A09-246-2 (2): Expressed in CHO—S cells, batch #1. A09-246-2 (3): Expressed in CHO—S cells, batch #2.

FIG. 2 shows sequence of the extracellular domain (fused to a 6 amino acid His tag, SEQ ID NO:29) of PD-L1. Peptides that could be identified by MS are indicated by grey bars. Those that showed protection from HD exchange in the presence of Fab are represented by black bars. Peptides that could not be analyzed are highlighted by underlining and italicizing in the sequence.

EXPERIMENTAL SECTION

Figure 3:
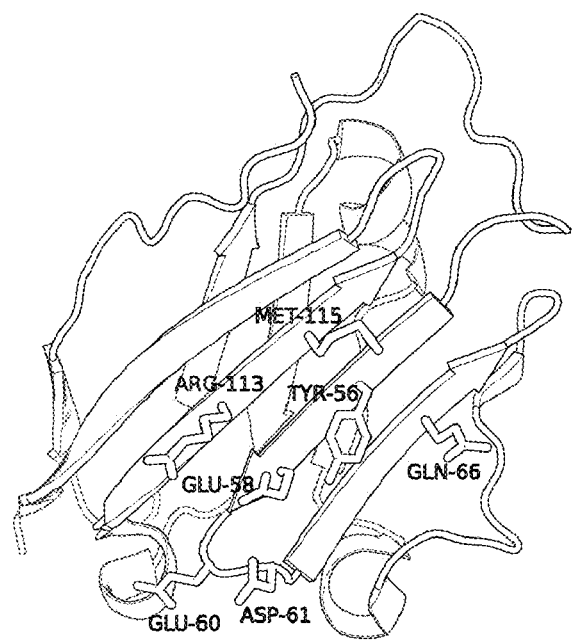
FIG. 3 shows the epitope of A09-246-2 on PD-L1. The backbone of PD-L1 is shown in a ribbon representation. Amino acids which, when mutated to alanine, destabilize the A09-246-2-PD-L1 binding by more than 0.7 kcal/mol are shown as sticks.
Figure 4:
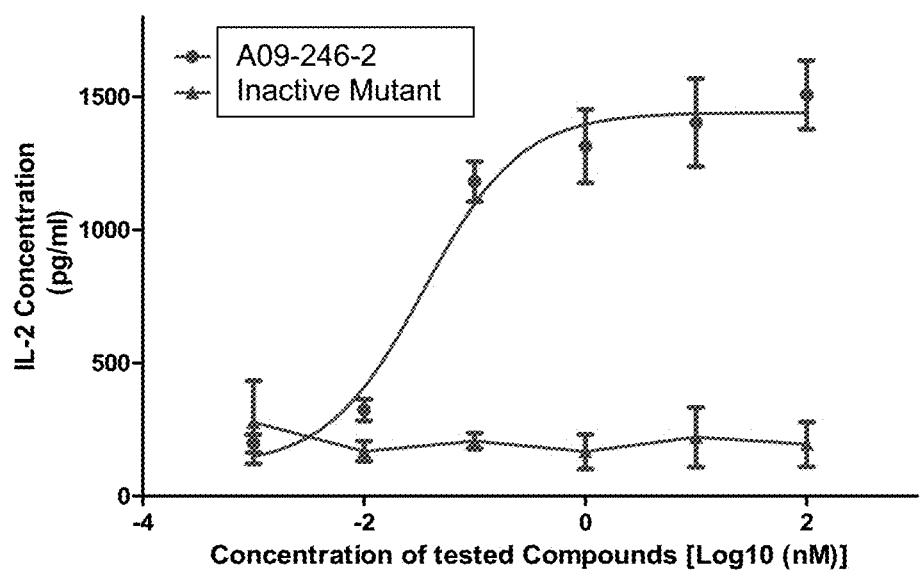
FIG. 4 shows that A09-246-2 efficiently enhances T cell activities represented by IL-2 production as shown by SEA human PBMC assay.
Figure 5:
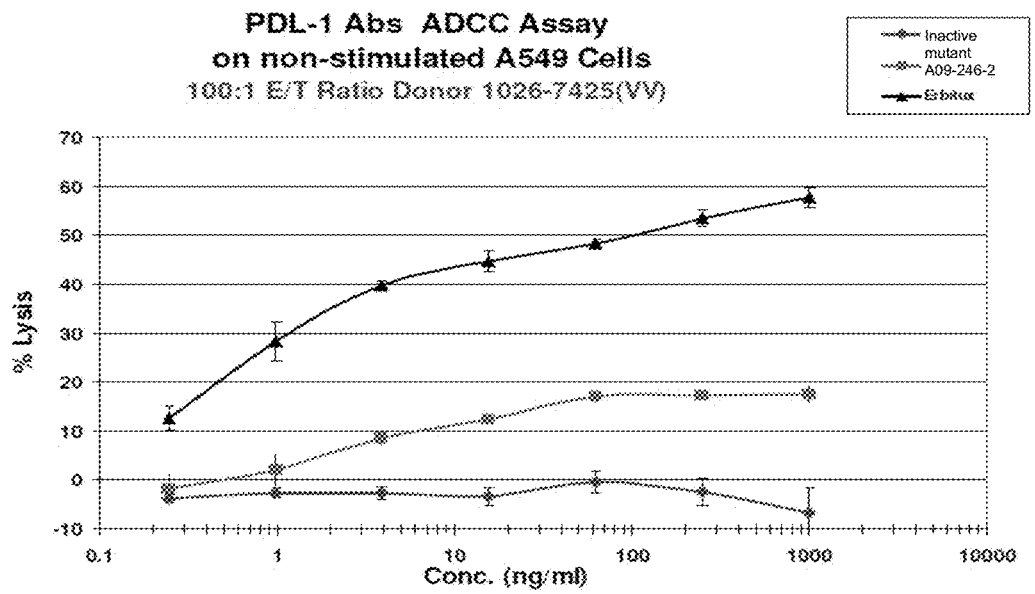
FIGS. 5-16 show that A09-246-2 increases ADCC in different tumor lines (stimulated and non-stimulated) and allotypes.
Figure 6:
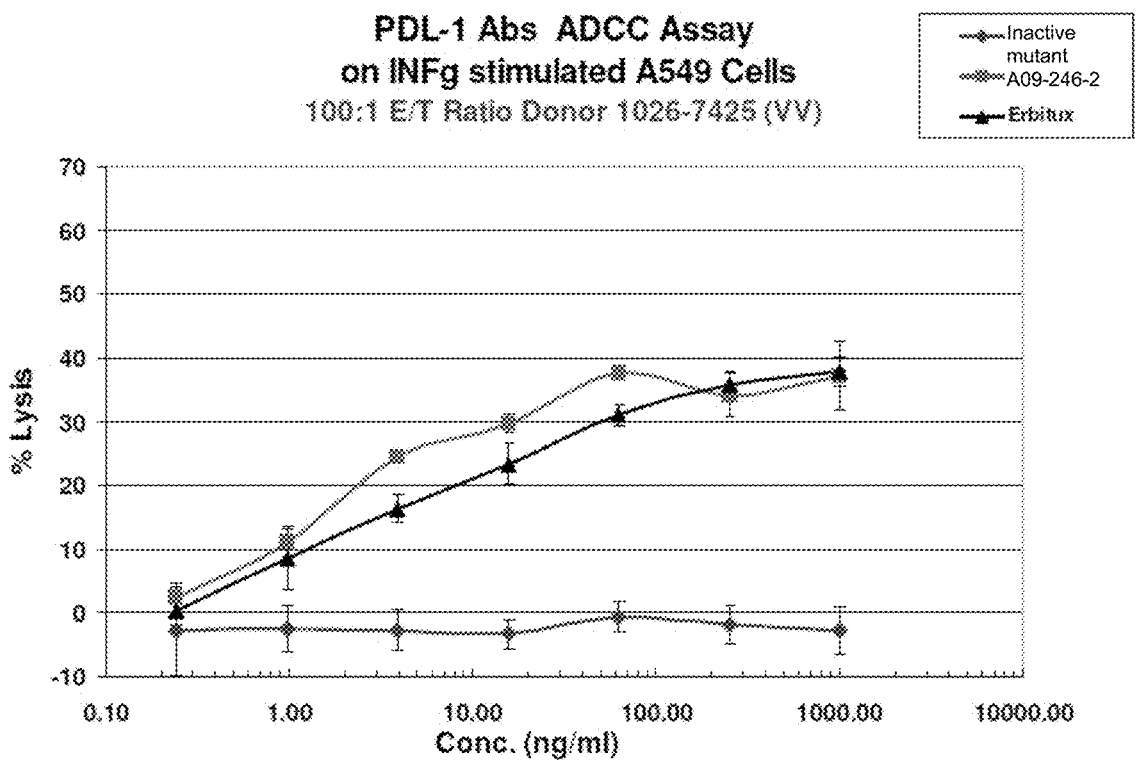
Figure 7:
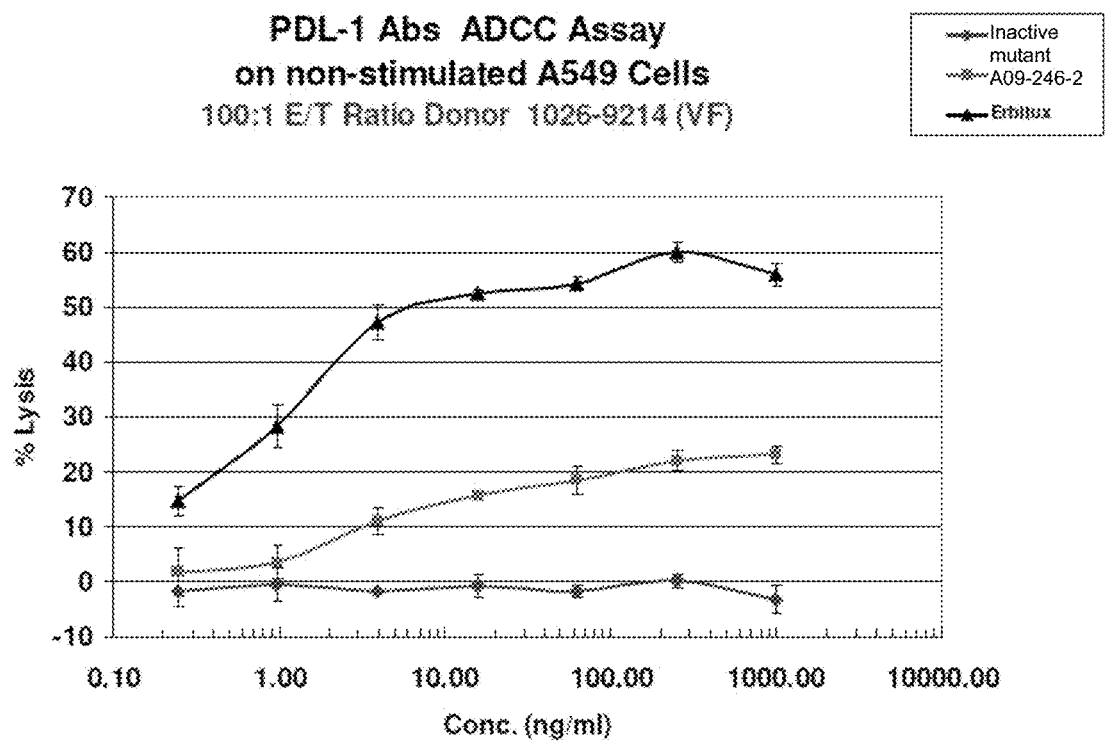
Figure 8:
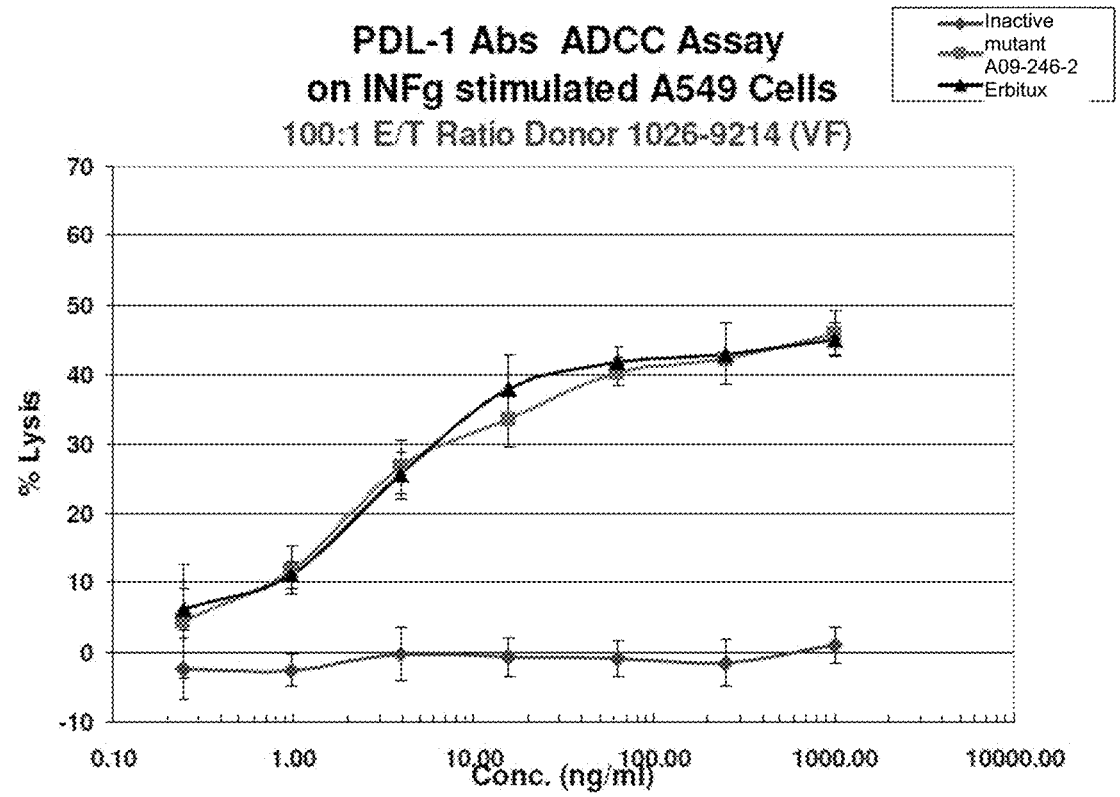
Figure 9:
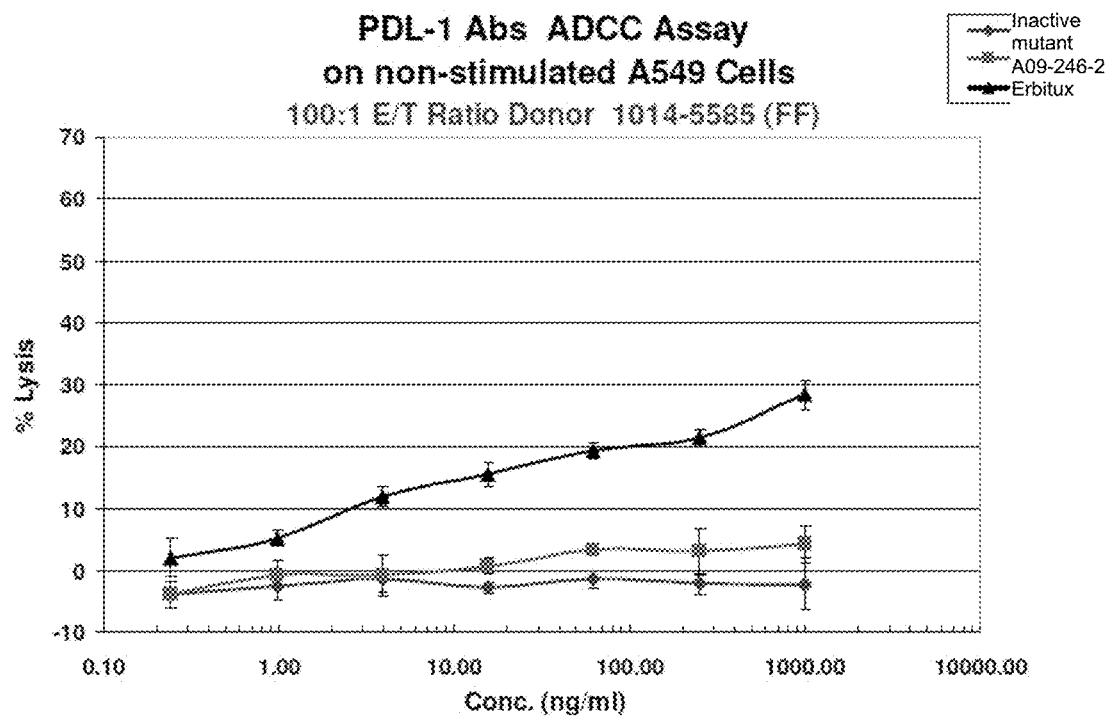
Figure 10:
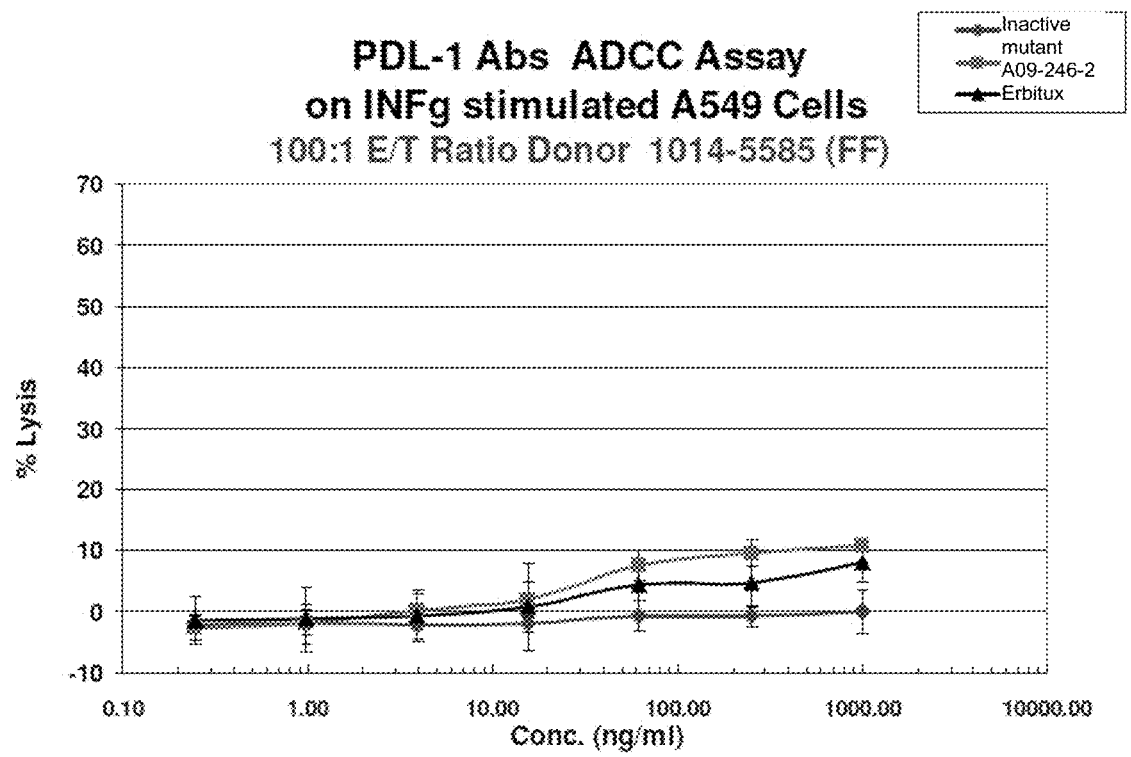
Figure 11:
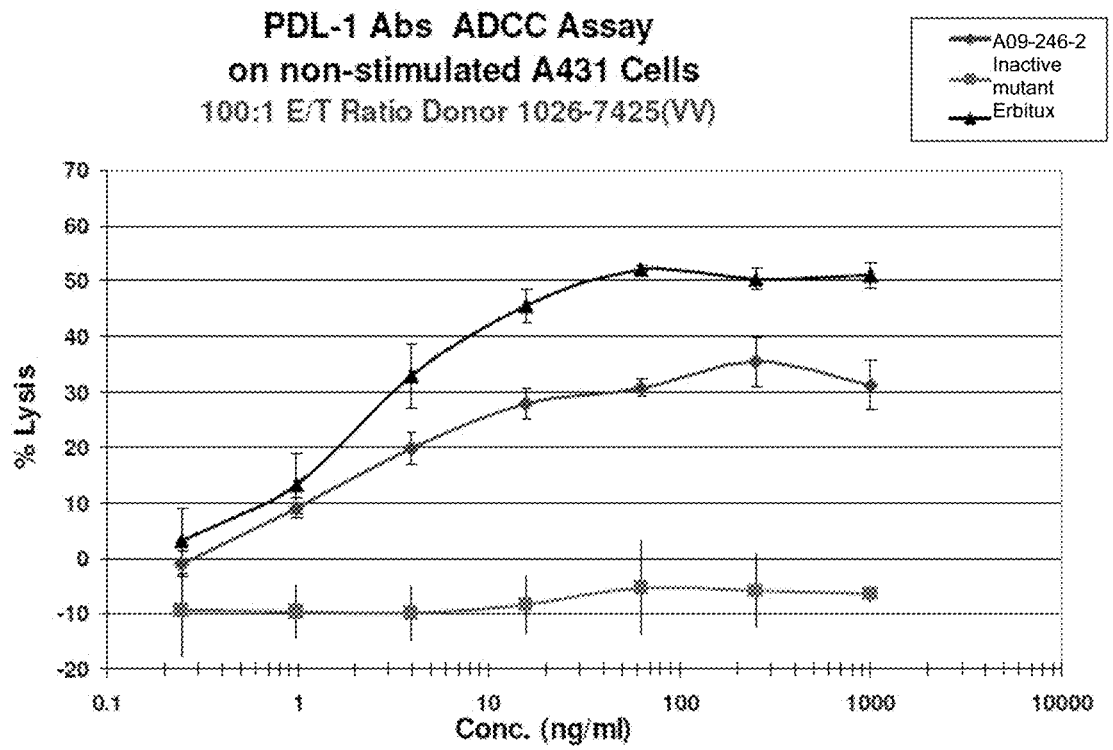
Figure 12:
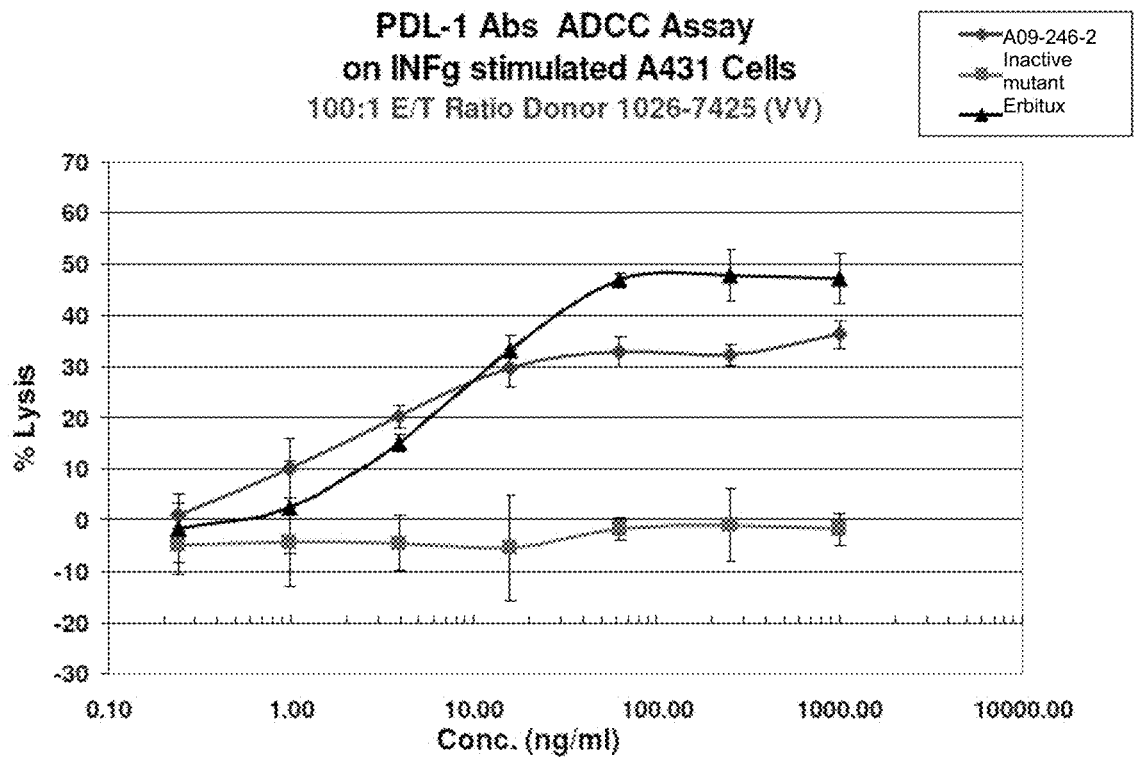
Figure 13:
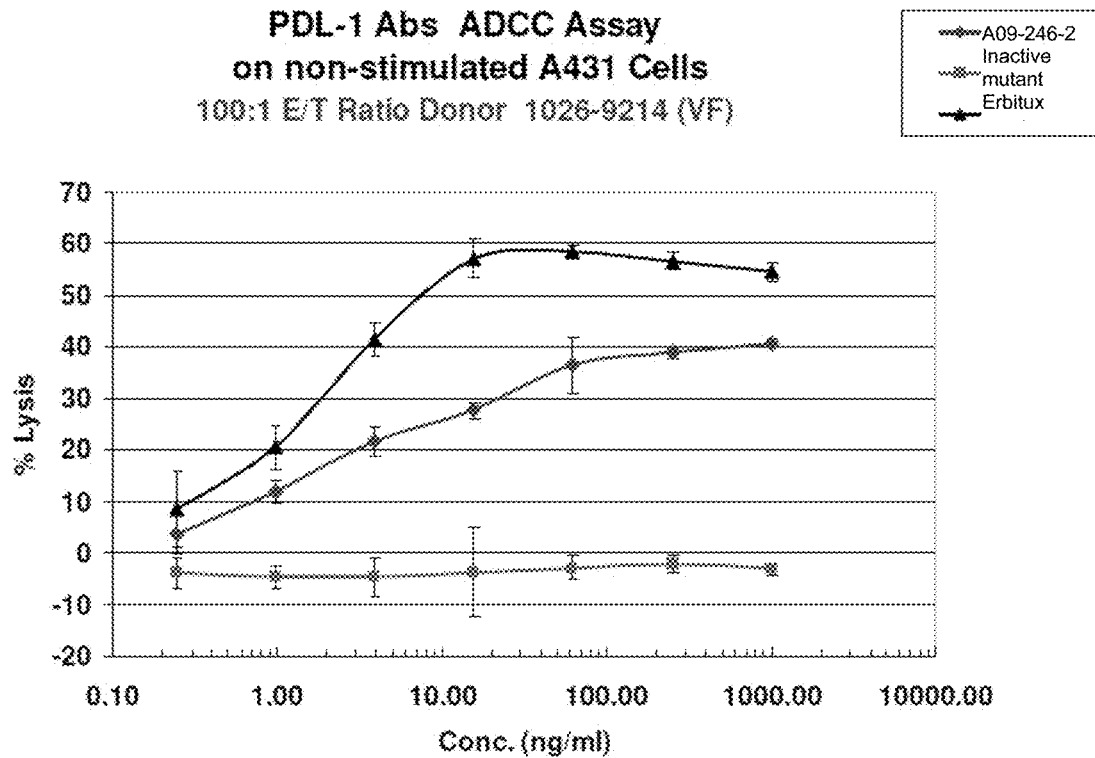
Figure 14:
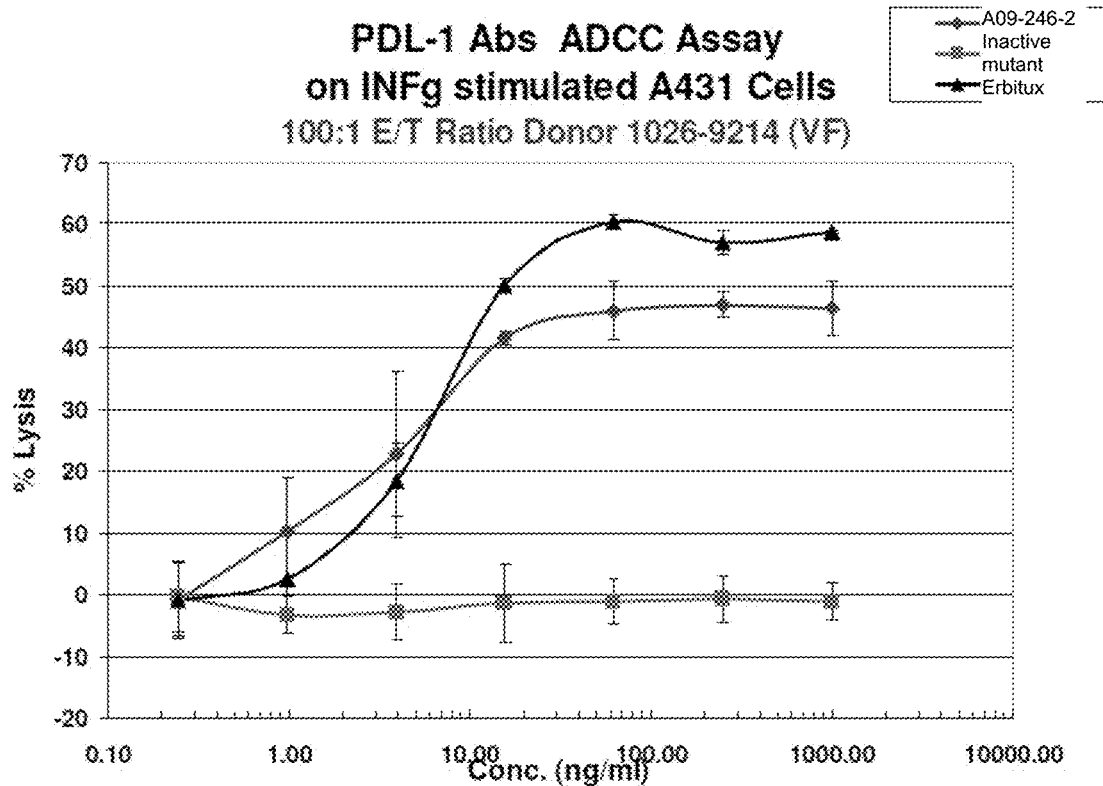
Figure 15:
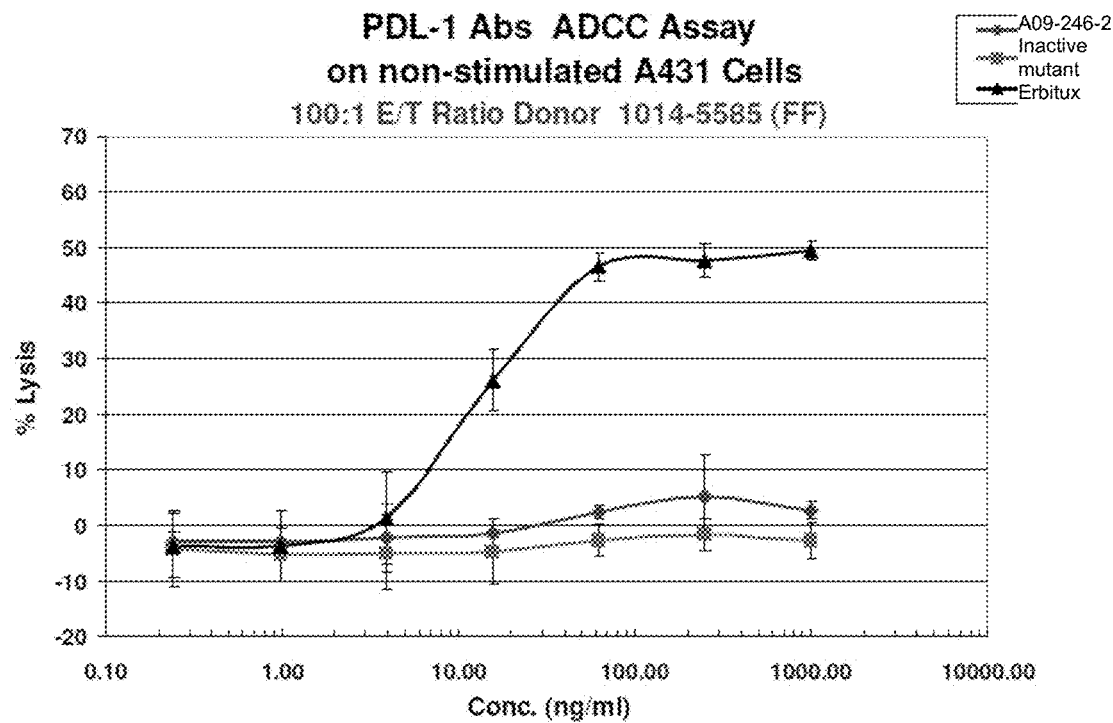
Figure 16:
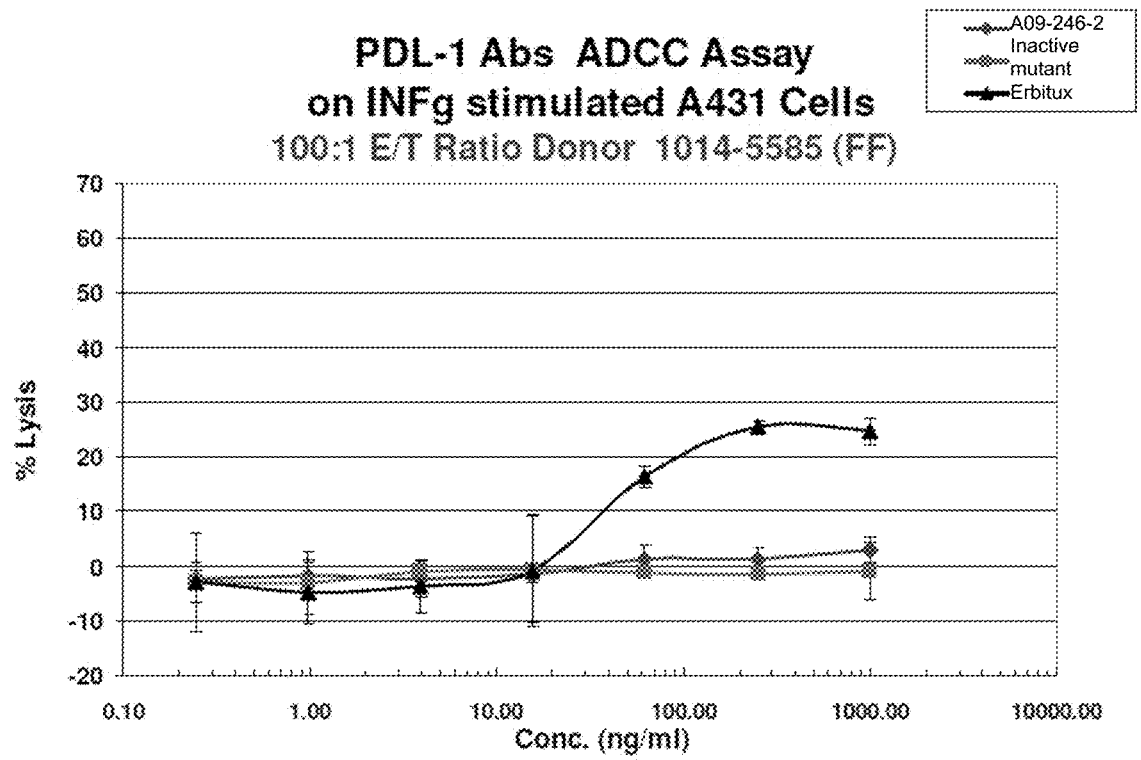

The working examples presented below are intended to illustrate particular embodiments of the invention, and are not intended to limit the scope of the specification or the claims in any way.

1. Selection and Improvement of Antibodies

Antibodies were selected from phage Fab display libraries. The selection included two different arms one utilizing biotinylated human PD-L1 on the different selection rounds and other alternating human and mouse PD-L1 as target on different rounds. 3840 clones were screened by ELISA to identify 170 individual PD-L1 binders. Based on the inhibition of PD-1 ligand binding, 48 hits were selected and were expressed in medium scale for further characterization.

The selected hits were reformatted and expressed as IgGs. Hit optimization candidates were selected based on the potency to block binding of PD-1 to PD-L1 and the ability of binding to both human and mouse versions of PD-L1. Binding to PD-L1 was originally determined by ELISA and later quantified by Biacore and binding to PD-L1 expressing cells by FACS. Four candidates fitted the predefined profile, including A09-188-1 which contained a lambda light chain.

A09-188-1 was chosen for affinity maturation and sequence optimization. The goals of the affinity maturation were increased affinity to the human target, cross-reactivity to the murine target, and improvement of manufacturability. Heavy chain mutations in the HVR's were introduced by codon based randomization. This heavy chain diversity was combined with light chain diversity introduced by light chain shuffling to generate the affinity maturation library. Further heavy and light chain FR and HVR residues were mutated to increase stability of the antibody and introduce amino acids found in the germline, such as the heavy chain FR mutation 193V.

This yielded the HVR sequences given below. It could be shown that at least the residues $X_1$-$X_{17}$ are variable in terms of target binding and have preferred meanings as herein disclosed.

HVR-H1 sequence is $X_1YX_2MX_3$ (SEQ ID NO:1);
HVR-H2 sequence is SIYPSGGX$_4$TFYADX$_5$VKG (SEQ ID NO:2);
HVR-H3 sequence is IKLGTVTTVX$_6$Y (SEQ ID NO:3);
wherein: $X_1$ is K, R, T, Q, G, A, W, M, I or S; $X_2$ is V, R, K, L, M or I; $X_3$ is H, T, N, Q, A, V, Y, W, F or M; $X_4$ is F or I; $X_5$ is S or T; $X_6$ is E or D
HVR-L1 sequence is TGTX$_7$X$_8$DVGX$_9$YNYVS (SEQ ID NO:8);
HVR-L2 sequence is $X_{10}VX_{11}X_{12}RPS$ (SEQ ID NO:9);
HVR-L3 sequence is SSX$_{13}$TX$_{14}$X$_{15}$X$_{16}$X$_{17}$RV (SEQ ID NO:10);
wherein: $X_7$ is N or S; $X_8$ is T, R or S; $X_9$ is A or G; $X_{10}$ is E or D; $X_{11}$ is I, N or S; $X_{12}$ is D, H or N; $X_{13}$ is F or Y; $X_{14}$ is N or S; $X_{15}$ is R, T or S; $X_{16}$ is G or S; $X_{17}$ is I or T.

2. Manufacturing, Purification and Formulation 2.1 Bioproduction and Clarification Antibody A09-246-2 corresponding to SEQ ID NO:32 (heavy chain) and SEQ ID NO:33 (light chain), was expressed from CHO—S cells transfected with the KOL isotype DNA sequence and sequence-optimized EU version, respectively. Cell cultures were conducted in batch mode in a 250 L Single-use-Bioreactor (SUB) (Table 2-2). Cells were grown in ProCHO5 growth media supplemented with 4 mM L-Glutamine±25 µg/mL puromycin at 37° C. The cultures were fed with 15% Efficient Feed B and 1.0 mM valproic acid 3 days after inoculation.

Crude conditioned media from the bioreactor runs were clarified using 1.1 m2 Millistak+ Pod D0HC (Millipore MD0HC10FS1) and 0.11 m2 Millistak+ Pod A1HC (Millipore MA1HC01FS1) filters, followed by terminal filtration with a Sartopore 2 filter (Sartorius 5445307H8-SS).

2.2 Purification

The purification process consisted of two chromatography steps, (a) MabSelect Protein A to capture the antibody from the clarified harvest, and (b) Hydroxyapatite Type II polish step to remove remaining aggregated product, host cell proteins and DNA, and product related impurities. An intermediate Q-filtration step was inserted between the 2 chromatography steps to further reduce DNA. SDS-PAGE and size exclusion chromatography SE-HPLC were used to analyze in-process samples during purification. Protein content of the Mabselect in-process samples was performed using the Protein A HPLC method while UV/Vis spectroscopy was used for all other process steps.

Post Mabselect eluates were subjected to 30 min of low pH viral inactivation (pH 3.7) and subsequently neutralized to pH 7.0 prior to the next purification step.

The final polishing step was the hydroxyapatite Type II chromatography. The conductivity of the Sartobind Q filtrate was adjusted to <3 mS/cm with water, and pH reduced to 6.5 with acetic acid before sample loading.

Bound anti-PD-L1 product was eluted with a NaCl step gradient. Aggregated product-related impurities was eluted with the Strip Buffer.

2.3 Formulation, Ultrafiltration and Diafiltration

Purified anti-PDL1 from the hydroxyapatite polishing step were concentrated and then diafiltered into their respective buffers according to the Table below. The bulk products were then sterile-filtered through 0.2 filter units and further diluted with formulation buffer to their final concentrations. Formulated bulk substance were further tested for endotoxin and checked by SE-HPLC.

| Formulation UF/DF | A09-246-2 |
|---|---|
| Starting Sample (mg) | 1279 |
| % Recovery | 100 |
| Final Concentration (mg/ml) | 10.2 |
| Purity (% Monomer) | 99 |
| Formulation Buffer | 10 mM sodium acetate, 140 mM sodium chloride, 0.05% (v/v) Tween 20, pH 6.0 |

2.4 Human Formulation

The following target administration and formulation profile was set:

Route of administration: iv infusion
Human dose range: 1-15 mg/kg
Concentration: 10 mg/ml
Storage conditions: liquid or frozen
Shelf life: more than 12 m The following liquid formulation was selected:
10.0 mg/mL A09-246-2
10 mM Acetate
5.1% (w/v) Mannitol
1.4 mM Methionine
0.05% (w/v) Tween 20
adjusted to pH 5.5

The formulation contains antioxidative excipients and was shown to be sufficiently stable at the following stress conditions:

Light stress
Shear stress
Freeze-thaw cycles
Oxidation stress

Stability was assessed at 2-8° C. and 25° C. up to 26 and 13 weeks, respectively. The formulation was found to be sufficiently stable at 2-8° C. up to the latest timepoint of 26 weeks. Also, a freeze-dried formulation was made with excellent stability at 25° C. up to 26 weeks.

3. Biochemical and Biological Characterization 3.1 Biacore Binding Affinity and Specificity Binding affinity and selectivity was determined by Biacore assays. The affinity of the lead antibody candidate for human and non human orthologues is summarized in the table below. The binding affinity of anti PD-L1 antibody A09-246-2 according to this invention for human, mouse and cynomolgus monkey proteins was statistically similar but highly reduced for dog, rat and rabbit proteins that displayed a very fast dissociation profile.

| PD-L1 | (ka 1/M s) | kd (1/s) | KD(M) | KD(nM) | +/− STDEV |
|---|---|---|---|---|---|
| Human | 2.72E+05 | 1.83E−04 | 6.73E−10 | 0.7 | 0.09 |
| Monkey | 2.49E+05 | 2.79E−04 | 1.12E−09 | 1.1 | 0.02 |
| Mouse | 1.77E+05 | 1.64E−04 | 9.26E−10 | 0.9 | 0.04 |
| Dog | 2.38E+06 | 1.07E−02 | 4.50E−09 | 4.5 | 0.4 |
| Rat | 3.54E+05 | 2.20E−02 | 6.68E−08 | 66.8 | 8.8 |
| Rabbit | 2.77E+05 | 2.82E−02 | 1.05E−07 | 105.4 | 11.2 |

The kinetic profiles for A09-188-1 and further mutants thereof are shown in the table below:

| Acc ID | anti-PD-L1 antibody | $K_D$ (nM) | t1/2 (min) | Relative $K_D$ |
|---|---|---|---|---|
| A09-188-1 | Antibody having a heavy chain according to SEQ ID NO: 34, and a light chain according to SEQ ID NO: 35 | 5.29 | 13.2 | 1.00 |
| | Heavy chain combination variants of A09-188-1 * | | | |
| A09-204-1 | VH-M31I, M33I, M35F, S63T, I93V | 0.10 | 578.2 | 0.02 |
| A09-211-1 | VH-M31I, M33L, M35F, S63T, I93V | 0.59 | 109.4 | 0.11 |
| A09-212-1 | VH-M33I, M35F, S63T, I93V | 0.22 | 254.4 | 0.04 |
| A09-213-1 | VH-M31I, M35F, S63T, I93V | 2.51 | 27.7 | 0.47 |
| A09-214-1 | VH-M31I, M33I, S63T, I93V | 0.40 | 179.1 | 0.08 |
| A09-215-1 | VH-M33L, M35F, S63T, I93V | 1.28 | 50.6 | 0.24 |
| A09-216-1 | VH-M31I, M33L, S63T, I93V | 0.91 | 77.8 | 0.17 |
| A09-219-1 | VH-M31S, M33I, M35F, S63T, I93V | 0.18 | 278.5 | 0.03 |
| A09-220-1 | VH-M31S, M33L, M35F, S63T, I93V | 0.78 | 68.3 | 0.15 |
| A09-221-1 | VH-M31S, M33I, S63T, I93V | 0.44 | 126.7 | 0.08 |
| A09-222-1 | VH-M31S, M33L, S63T, I93V | 1.24 | 47.1 | 0.23 |
| A09-223-1 | VH-M31S, M35F, S63T, I93V | 3.62 | 13.5 | 0.68 |
| | Light chain variant of A09-188-1 * | | | |
| A09-202-1 | VL-A31G | 4.15 | 18.8 | 0.78 |
| | Heavy and light chain combination variants of A09-188-1 * | | | |
| A09-248-2 | VL-A31G; VH-M31I, M33I, M35F, S63T, I93V | 0.10 | 436.4 | 0.02 |
| A09-239-2 | VL-A31G; VH-M31I, M33L, M35F, S63T, I93V | 0.36 | 119.7 | 0.08 |
| A09-240-2 | VL-A31G; VH-M33I, M35F, S63T, I93V | 0.16 | 245.9 | 0.03 |
| A09-241-2 | VL-A31G; VH-M31I, M33I, S63T, I93V | 0.32 | 166.4 | 0.07 |
| A09-242-2 | VL-A31G; VH-M33L, M35F, S63T, I93V | 0.76 | 55.6 | 0.16 |
| A09-243-2 | VL-A31G; VH-M31I, M33L, S63T, I93V | 0.63 | 85.0 | 0.13 |
| A09-244-2 | VL-A31G; VH-M31S, M33I, M35F, S63T, I93V | 0.12 | 279.7 | 0.03 |
| A09-245-2 | VL-A31G; VH-M31S, M33L, M35F, S63T, I93V | 0.43 | 77.2 | 0.09 |
| A09-246-2 | VL-A31G; VH-M31S, M33I, S63T, I93V | 0.34 | 125.4 | 0.07 |
| A09-247-2 | VL-A31G; VH-M31S, M33L, S63T, I93V | 0.76 | 57.8 | 0.16 |

(*) Amino acid positions counted from the N-terminus of the heavy and light chains, respectively

3.2 Selectivity

Selectivity was determined by evaluating the binding to members of the B7 family including hu-PD-L1-huFc, hu-PDL-2-huFc, hu-B7.1-huFc, hu-B7.2-huFc, huB7-H2-huFc and huB7-H3-huFc by Biacore.

All the anti-huPD-L1 MAb tested including A09-246-2 reacted specifically with only huPD-L1 protein and not with any other B7 Family proteins.

3.3 PD-L1 PD-1 Interaction Blocking

The ability of A09-246-2 and a control antibody to compete with the binding of radio-labelled PD-L1 to immobilized PD-1 was determined by radioactive competitive displacement assay. FIG. 1 shows representative competition curves for the test antibodies. The results demonstrated that A09-246-2 efficiently blocks the interaction of PD-1 and PD-L1 with an IC50 of 0.071±0.008 nM (0.01±0.001 µg/ml).

The follow assay protocol was used:
1. Add 60 ml/well of PBS, containing 1 mg/ml of human PD-1Fc (R&D Systems, 1086-PD; lyophilized PD-1 dissolved with PBS at 200 mg/ml) to white Costar plates (Corning 3922). Incubate overnight at 4° C.
2. Rinse wells 1 time with PBS.
3. Block wells with 120 ml of 0.5% BSA (Sigma A-3059) dissolved in binding buffer, for 1 h at room temperature (RT).
4. Rinse wells 1× with binding buffer.
5. Add 50 ml of test sample to wells (antibody, supernatant). Dilute antibodies to 20 nM in assay buffer and serial dilute 9× at a 1:4 dilution. Samples are diluted to 2× final concentration, prior to adding to the wells (usually starting at 10 nM-1× concentration).
6. Nonspecific binding: add 50 ml of PD-L1/Fc (R&D Systems, 156-B7) at a final concentration of 250 nM in place of the test sample at a 500 fold excess to the labeled PD-L1. Total wells receive the same volume of assay buffer.
7. Add 50 ml of 0.5 nM $^{125}$I-PD-L1 (custom labeled at Perkin Elmer, lot number CIS32211, 250 nM, 2400 Ci/mmol) to each well. Dilute to 2× the final concentration in assay buffer–final concentration=0.25 nM.
8. Shake the plate for 2-2.5 h at 37° C.
9. Wash the wells 5 times with cold binding buffer.
10. Add 100 ml of Microscint 20 (Packard 6013641) to each well. Incubate for at least one h at RT.
11. Count luminescence on Topcount ($^{125}$I-Microscint protocol).

Binding Buffer: 50 mM Hepes, pH 7.5, 130 mM NaCl, 5.1 mM KCl, 1.3 mM $MgSO_4$

Assay buffer: binding buffer+0.5% BSA

3.4 PD-L1 B7.1 Interaction Blocking

The ability of A09-246-2 to block soluble B7.1 binding to PD-L1 on cell surface was measured by FACS. Results indicated A09-246-2 efficiently blocks the interaction of B7.1 and PD-L1 with an IC50 of 0.2±0.004 nM (0.03±0.0006 µg/ml).

3.5 Epitope Mapping a) Hydrogen-Deuterium Exchange

The extracellular domain of PD-L1 antigen (SEQ ID NO:29) was incubated in heavy water ($D_2O$) solution to allow amide protons on the protein backbone to exchange with deuterons from the solvent, in either the presence or absence of excess anti-PD-L1 Fab or a non-specific Fab. The samples were digested with protease and analysed by liquid chromatography-mass spectrometry (LC-MS) to determine the level of deuteration in each peptide.

The Fab corresponding to A09-246-2 was used instead of the full IgG in order to simplify the mass spectrometry analysis by decreasing the number of peptides generated by protease digestion. Despite this, some regions remained that could not be identified and analyzed (underlined, italicized sequence portions in FIG. 2), however these regions represent a small fraction of the sequence, and mostly reside in the second immunoglobulin domain, distant from the epitope containing region.

Residues 32-39 in domain I of the extracellular domain were also resistant to identification by mass spectrometry and encompass the site of an N-linked glycosylation; as A09-246-2 is known to bind an aglycosylated version of PD-L1 produced in E. coli, the inability to analyze this peptide for HD exchange rates was not of concern.

Several peptides from antigen were observed to have a significantly reduced rate of exchange of protons for deuterons in the presence of Fab than in its absence, suggesting that at least some residues from these peptides are in direct contact with the Fab and constitute a conformational epitope (FIG. 2). Although the two peptides showing protection from solvent are far apart in the primary sequence (underlined, bold print in FIG. 2, they are proximal in the threedimensional structure of PD-L1 and constitute each a single binding patch on the surface of the antigen (see FIG. 3).

In summary, HD exchange identified two peptides
(i) residues 36-48 in FIG. 2 (extracellular domain plus His tag, SEQ ID NO:29), corresponding to residues 54-66 of the full length sequence (SEQ ID NO:28)
(ii) residues 94-104 in FIG. 2 (SEQ ID NO:29), corresponding to residues 112-122 SEQ ID NO:28
that form a conformational epitope on PD-L1 and that contains the functional epitope of A09-246-2.

b) Mutagenesis

To obtain a finer, residue-level mapping of the epitope and to complement the HD exchange data, molecular modelling and manual inspection of the crystal structure of PD-L1 (Lin, D. Y.-W. et al. PNAS 105, 3011-6 (2008); PDB record 3BIK) was used to select solvent exposed residues within and around the epitope identified by HD exchange. The selected residues were mutated either to alanine (large to small) or to another, potentially more disruptive amino acid (small to large).

In total, 48 point mutants were designed, expressed and purified from HEK cells, and tested for binding to A09-246-2 using surface plasmon resonance (SPR). Binding hotspots, or residues that contribute most to the binding energy (Wells. J. A., *PNAS* 93, 1-6, 1996), were identified as those that did not meet a threshold binding signal at 100 nM antigen. Furthermore, the affinity of the antibody for wild-type and each mutant was determined and used to calculate the contribution of each epitope residue to the binding energy.

The results are summarized in the table below, where 48 point mutants of PD-L1 were compared to wild-type PD-L1 antigen for antibody binding. SPR (Biacore) was used to perform a kinetic study allowing determination of kinetic rate constants ($k_a$ and $k_d$). Briefly, goat polyclonal anti-human Fc antibody was chemically coupled to a CM5 chip. A11-128 was injected next and captured by the polyclonal. Buffer was used to wash out unbound antibody until the baseline RU stabilized. Antigen (wild-type or mutant PD-L1) was next injected at a fixed concentration for 3 minutes and the association was recorded. Buffer was injected for a further 3 minutes and dissociation was observed. The antigens were injected at concentrations of 100 nM, 50 nM, 25 nM, 12.5 nM and 6.25 nM (except for Y56 and D61 mutants, which were injected at 1 uM, 500 nM, 250 nM, 125 nM and 62.5 nM). Between each cycle, the chip was regenerated with low pH buffer and fresh A09-246-2 was captured prior to injecting the next concentration of antigen. The rate constants were determined by iterative fitting of the data to a 1:1 binding model by an algorithm that minimizes Chi-squared. The equilibrium dissociation constant ($K_D$) was calculated as the ratio of the kinetic constants and the change in the Gibbs free energy of binding of mutant relative to wild-type PD-L1 ($\Delta\Delta G_{mut}$) was derived from the ratio of the wild-type and mutant $K_D$s. The free energy changes are highlighted according to destabilization of antibody-antigen binding; "**": >3 kcal/mol destabilization (binding hotspots); "*": >0.7 kcal/mol. Mutants at Y56 had such a low affinity that the $K_D$ could be accurately measured and the minimum $K_D$ is given instead. For D61A no binding could be found. According to this analysis, amino acids marked with "**" or "*" are part of the functional epitope. The temperature midpoint of fluorescently monitored thermal denaturation is given for the wild type and mutant proteins. ND: Not Determined; BP: Biphasic. The qualitative appearance of the wild type and mutant proteins on size exclusion chromatography (SEC) is also given. M: monodisperse and the same elution volume as wild type; M/T: peak at the same elution volume as wild type but with an additional tail. For $K_D$ and $T_{1/2}$, the mean and standard deviation is given where n>1.

| Mutation | $\Delta\Delta G_{mut}$ (kcal/mol) | $K_D$ (nM) | $T_{1/2}$ (° C.) | SEC |
|---|---|---|---|---|
| PDL-1 | 0.00 | 0.55 +/− 0.21 | 59.1 | M |
| T20A | −0.19 | 0.39 +/− 0.15 | 52.5 +/− 0.2 | M |
| D26A | −0.44 | 0.26 +/− 0.19 | 52.8 +/− 0.2 | M |
| L27A | −0.07 | 0.48 +/− 0.68 | 51.7 +/− 0.5 | M |
| E45A | −0.54 | 0.22 | 58.0 | M |
| K46A | −0.28 | 0.34 +/− 0.10 | 51.6 | M |
| Q47A | 0.04 | 0.59 +/− 0.27 | ND | M |
| D49A | −0.25 | 0.36 +/− 0.04 | BP (>49) | M |
| A51Q | 0.09 | 0.63 +/− 0.32 | 57.3 +/− 0.6 | M |
| A52R | −0.84 | 0.13 +/− 0.04 | 55.2 | M |
| I54A | −1.28 | 0.06 +/− 0.09 | 57.2 +/− 2.5 | M |
| I54K | 0.62 | 1.57 +/− 0.19 | 57.2 | M |
| Y56A | >4** | >1 uM | 57.5 +/− 0.7 | M |
| Y56K | >5** | >4 uM | 55.4 +/− 1.3 | M |
| E58A | 1.90* | 13.58 +/− 0.59 | 54.6 +/− 0.6 | M |
| E60A | 1.45* | 6.32 +/− 0.44 | 50.4 | M |
| D61A | infinite** | >5 uM | 52.0 | M |
| K62A | 0.49 | 1.26 +/− 0.07 | ND | ND |
| N63A | 0.21 | 0.78 +/− 0.18 | ND | M |
| Q66A | 0.86* | 2.35 +/− 0.23 | ND | M |
| V68A | 0.02 | 0.57 +/− 0.04 | ND | M |
| V68R | 0.55 | 1.37 +/− 0.05 | 56.0 | M/T |
| H69Q | 0.01 | 0.56 +/− 0.06 | ND | M |
| E71A | −0.25 | 0.36 +/− 0.11 | 52.8 +/− 1.5 | M |
| D73A | −0.14 | 0.43 +/− 0.01 | 53.5 +/− 2.1 | M |
| K75A | −0.57 | 0.21 +/− 0.06 | 57.7 +/− 1.8 | M |
| V76A | −0.49 | 0.24 +/− 0.06 | 55.7 | M |
| H78A | 0.10 | 0.65 +/− 0.01 | 56.6 +/− 0.6 | M |
| S79A | −0.03 | 0.52 +/− 0.21 | 56.3 +/− 0.9 | M |
| S79E | −0.36 | 0.30 +/− 0.09 | 60.0 | M |
| S80A | 0.07 | 0.61 +/− 0.05 | 57.0 | M |
| S80E | 0.16 | 0.71 +/− 0.15 | 56.8 +/− 4.5 | M |
| R82A | −0.23 | 0.37 +/− 0.16 | 51.2 +/− 0.4 | M |
| K105A | −0.19 | 0.40 +/− 0.08 | 57.0 +/− 1.5 | M |
| Q107A | −0.13 | 0.44 +/− 0.03 | 58.6 +/− 2.0 | M/T |
| A109E | −0.03 | 0.52 +/− 0.04 | 54.0 | M |
| V111A | −0.42 | 0.27 +/− 0.03 | 50.2 +/− 0.2 | M |
| V111E | −0.39 | 0.28 +/− 0.07 | 51.6 +/− 0.0 | M |
| R113A | 1.53* | 7.22 +/− 0.26 | 56.7 | M |
| M115A | 0.97* | 2.79 +/− 0.17 | 51.4 +/− 0.1 | M |
| S117A | −0.60 | 0.20 +/− 0.04 | 52.7 +/− 0.3 | M |
| A121R | −0.10 | 0.46 +/− 0.20 | 54.0 +/− 0.5 | M |
| D122A | −0.13 | 0.44 +/− 0.02 | ND | M |
| Y123A | 0.40 | 1.07 +/− 0.05 | ND | M |
| K124A | 0.10 | 0.65 +/− 0.09 | 53.1 +/− 0.6 | M |
| R125A | 0.41 | 1.09 +/− 0.04 | 51.8 +/− 0.2 | M |
| T127K | −0.25 | 0.36 +/− 0.01 | 54.0 | M |
| T127A | −0.13 | 0.44 +/− 0.03 | 51.4 +/− 0.0 | M |
| K129A | −0.21 | 0.38 +/− 0.18 | 50.8 +/− 1.2 | M |

It was important to confirm that the lack of binding to A09-246-2 of the Y56A, Y56K and D61A point mutants was indeed due to loss of hotspot residues and not to global unfolding of the antigen. The structural integrity of the mutated proteins was confirmed using a fluorescence monitored thermal unfolding assay in which the protein is incubated with a dye that is quenched in aqueous solution but fluoresces when bound by exposed hydrophobic residues. As the temperature increases, thermal denaturation of the protein exposes the hydrophobic core residues and this can be monitored by an increase in fluorescence of the dye. Mutants of Y56 or D61 all display a two state transition similar to wild-type PD-L1, indicating a folded structure at room temperature. The data were fit to equation 1 (adapted from Bullock, A. N. et al. Thermodynamic stability of wild-type and mutant p53 core domain. *PNAS* 94, 14338-14342 (1997)) to determine the temperature at the inflection point of the curve ($T_{1/2}$).

$$F = \frac{\{Fi + \beta i * T + ((F\max + \beta\max * T) * e^{[m*(T-T1/2)]})\}}{1 + e^{[m*(T-T1/2)]}}$$ Equation 1

Mutants of Y56 and D61 displayed minimal destabilization of the antigen indicated by a small decrease in the $T_{1/2}$ of fluorescence monitored unfolding (table above). This confirms that Y56 and D61 are true binding hotspots for A09-246-2. The structural integrity of most of the other mutant proteins was also confirmed by this method (table above). The observation that most mutant proteins behaved similarly to wild type on analytical size exclusion chromatography (last column in the above table) provides further support for native structure of mutant antigen proteins.

3.6 Binding to Tumor Cells and Primary Cells

The binding of A09-246-2 to PD-L1 on the surface of tumor cells as well as on primary human and experimental animal cells was confirmed by a FACS assay. A09-246-2 demonstrated reactivity to human PD-L1 on all seven tested human tumor lines (A431, epithelial carcinoma cell line; A549, lung adenocarcinoma epithelial cells; BxPC3, pancreatic cancer cells; HCT116, colorectal carcinoma; M24, melanoma cell lines; PC3 mm2, prostate cancer cell line; U-87 MG, glioblastoma-astrocytoma) of which PD-L1 was up-regulated by interferon treatment to enable detection. Because primary PBMC have low levels of PD-L1 expression which is difficult to be detected, human PBMC or PBMC from dog, rabbit and rat were all subjected to PHA stimulation for 2 days. A09-246-2 demonstrated reactivity to PD-L1 on human and animal primary cells.

3.7 EC50 Measured by Direct FACS Binding Assay

The dose dependent binding ability of A09-246-2 to the target on the cell surface was confirmed by FACS. A09-246-2 efficiently binds to human PD-L1 expressed on the HEK cell surface with an EC50 of 0.3±0.02 nM (0.04±0.003 µg/ml); to cynomolgus monkey expressed on the HEK cell surface with an EC50 of 0.94±0.015 nM (0.14±0.002 µg/ml); to mouse PD-L1 expressed on the HEK293 cell surface with an EC50 of 0.34±0.08 nM (0.05±0.012 µg/ml) and mouse PD-L1 expressed on the EL4 cell surface with an EC50 of 0.91±0.21 nM (0.13±0.03 µg/ml). The assays qualitatively described the dose dependent binding characteristics of anti-PD-L1.

3.8 Activity in Cellular Assays

Currently there is no scientific evidence that the engagement of PD-L1 with it ligands transduces stimulatory signalling through PD-L1 into the PD-L1 expressing cells, therefore the developed assays employed T cell activation in the procedures. The ability of anti-PD-L1 antibody to enhance T cell immuno-responses was measured in vitro in cellular assays using murine T cells or human PBMC.

a) OT-1 Assay

Antigen-specific CD8 T cells were generated by stimulating splenocytes from OT-1 transgenic mice with Ova peptide SIINFEKL and cryopreserved. mPD-L1 over-expressing EL4 cells were used as antigen presenting cells. Serial dilutions of tested compounds were incubated with thawed OT-1 T cells and SIINFEKL-loaded APC for 48 hours. IFN-γ in the supernatant was measured using mIFN-γ ELISA. Anti-PD-L1 (A09-246-2) efficiently enhanced T cell activities represented by IFN-γ production with an EC50 of 0.28±0.1 nM (0.04±0.015 µg/ml)

b) SEA Assay

During the human PBMC assay development, it could be demonstrated that only anti-PD-L1 treatment did not trigger IL-2 or IFN-γ production in the absence of T cell activation and did not enhance IL-2 production in the presence of optimal activation either. The ability of anti-PD-L1 to enhance IL-2 production by T cells responding to super antigen activation was assessed. Super antigen such as Staphylococcal enterotoxin A (SEA) is able to crosslink the T cell receptor (TCR) and MHC class I to activate CD4 T cells. The dose dependent activity of A09-246-2 to enhance T cell functions was assessed upon such activation. Serial dilutions of A09-246-2 were incubated with human PBMC in the presence of SEA for 96 hours. Human IL-2 in the supernatant was measured using human IL-2 ELISA. Results indicated anti-PD-L1 efficiently enhanced T cell activities represented by IL-2 production with an EC50 of 0.08±0.03 nM (0.012±0.005 µg/ml)

3.9 Antibody Dependent Cell-Mediated Cytotoxicity (ADCC)

ADCC was measured utilizing two different human tumor lines A431 and A549 as target cells and human PBMC as effector cells. In some cases, tests were performed using target cells following stimulation with Interferon-gamma to increase the expression of PD-L1. The anti-EGFR antibody, cetuximab, was used as an ADCC positive control. Given the fact that the FcγIIIα receptor 158V allotype displays a higher affinity for human IgG1 and increases ADCC, the observed results were correlated with the donor's allotype.

ADCC activity of A09-246-2 was comparable to that mediated with the anti-EGFR antibody cetuximab, inducing approximately 50% of maximum lysis in both cell lines. INF-γ treatment did not alter the response of A431 cells for all the different allotypes tested (V/V, V/F and F/F). A significant difference (almost twice) between stimulated and not stimulated cells was observed when A549 cells were employed for PBMC from V/V and V/F donors. No ADCC was observed when PBMC from F/F donors were analyzed with A549 cells.

4. In Vivo Activity

In the studies presented here, the efficacy of PD-L1 antibody (Ab) blockade against various murine tumor models was investigated. Inhibition of the PD-1/PD-L1 interaction is proposed to exert a therapeutic effect by restoring anti-tumor CD8$^+$ T cell responses, thus all of the preclinical efficacy studies were conducted in syngeneic murine tumor models in which the immune system of the host is fully intact. To circumvent the need for a surrogate antibody, the antibody used in the studies was specifically selected for cross-reactivity to murine PD-L1. However, because the antibody is fully human, neutralizing immunogenicity is elicited in mice, which limits the effective dosing window to a seven day period. Despite this significant dosing limitation, the selected antibody has demonstrated significant activity as a monotherapy and in various combination therapy settings. The anti-tumor activity of the anti-PD-L1 antibody demonstrated a dose-dependent trend when given as a monotherapy against MC38 tumors.

Immunohistochemical analysis of PD-L1 expression within responsive and non-responsive tumor models revealed a strong link between the level of PD-L1 expression and the level of anti-tumor efficacy. To confirm the proposed mechanism of action (MOA), a study was conducted in MC38 tumor bearing mice that were systemically depleted of CD8+ T cells. In animals depleted of CD8+ T cells, the efficacy of anti-PD-L1 therapy was completely abrogated, confirming that cytotoxic T lymphocyte (CTL) effector function is responsible for the inhibition of tumor growth. To evaluate the combination potential of anti-PD-L1 therapy, combination partners were selected known to elicit anti-tumor T cell responses or otherwise enhance the effects of immunotherapy. In combination with fractionated radiotherapy against MC38 tumors, the anti-PD-L1 antibody showed strong synergistic activity, with curative potential. Combination with a single low-dose of cyclophosphamide resulted in enhanced anti-tumor effects in the MC-38 model that were associated with an increased frequency of tumor-antigen specific CD8+ T cells. Anti-PD-L1 therapy significantly extended survival time when combined with Gemcitabine in the PANC02 orthotopic tumor model of pancreatic cancer. When anti-PD-L1 was combined with cyclophosphamide pre-treatment followed by vaccination with Stimuvax, a significant increase in tumor growth inhibition was achieved in both the MC38/MUC1 and PANC02/MUC1 tumor models. Significantly enhanced efficacy was also observed when the anti-PD-L1 antibody was combined with the core components of the FOLFOX chemotherapy regimen. Thus, several promising combination approaches for anti-PD-L1 therapy were successfully identified, including three "standard of care" treatment regimens (radiation therapy; FOLFOX; Gemcitabine).

Mechanistic data derived from these studies demonstrated that anti-PD-L1 therapy is consistently associated with increased percentages of CD8+ T cells, CD8+ T effector memory cells, and PD-1CD8+ T cells in the spleens and tumors of treated mice.

4.1 Dose-Response in MC38 Tumor Model and Combination with CPA

In this study, mice were inoculated subcutaneously in the right flank with $1 \times 10^6$ MC38 colon carcinoma cells. When tumors reached a mean volume of ~50 mm³, mice were sorted into treatment groups (N=14) (defined as study day 0). Groups were administered A09-246-2 intravenously at dose levels of 100, 200, 400, or 800 µg on days 0, 3, and 6. A control group was treated with 200 µg of an inactive isotype antibody. Tumors were measured twice weekly for the study duration. All treatment groups demonstrated significant efficacy (P<0.050) when compared to the isotype control group. Although the 800 µg dose group did not show enhanced efficacy over the 400 µg group, a significant trend toward a dose-dependent effect was observed. In a second dose-response study that followed the same design, a general trend toward dose-dependent activity was again observed. However, the 800 µg dose group in that particular study showed significantly lower anti-tumor activity than did the 400 µg dose group. The lack of increased efficacy at doses above 400 µg may indicate an efficacy plateau as a result of target saturation, or a stronger immunogenic effect may occur at higher doses, resulting in lower drug exposure. Additionally, these studies explored the efficacy of anti-PD-L1 in combination with pre-treatment with a low, immunomodulatory dose of cyclophosphamide (CPA). The CPA combination was observed to significantly improve the efficacy of low doses of anti-PD-L1 (100 µg), and this effect was associated with increased frequencies of p15E tumor antigen-specific CD8+ T cells as determined by ELISPOT.

Immunophenotyping data from these studies revealed that anti-PD-L1 therapy is associated with significantly increased percentages of various CD8+ T cell subsets in spleens: total CD8+ T cells, p15E tumor antigen-specific CD8+ T cells, PD-1CD8+ T cells, and CD8+ T effector memory ($T_{EM}$) and CD8+ T central memory ($T_{CM}$) cells. Increased intratumoral accumulation of CD8+ T cells and CD8+ $T_{EM}$ cells was also observed. These observations support htat anti-PD-L1 therapy as an effective strategy for driving anti-tumor CD8+ T cell responses.

4.2 Efficacy in C1498/GFP Disseminated Leukemia Model

To create the disseminated leukemia model, C4198-GFP leukemia cells ($2 \times 10^4$) were injected i.v. into C57BL/6 mice on day 0. Mice were then randomized into treatment groups (N=5) that received either a 400 µg dose of anti-PD-L1 Ab (A09-246-2) or an equivalent dose of an inactive isotype antibody on days 1, 4, and 7 by i.p. injection. The primary endpoint of this study was survival based on the onset of clinical signs, indicative of metastatic dissemination, which warranted euthanasia. At the end of the study (day 76), 20% of mice (⅕) were still alive in the isotype antibody treated group, and 80% (⅘) survivors remained in the A09-246-2 treated group.

4.3 Combination with Gemcitabine in the PANC02 Orthotopic Model

Three separate studies were conducted to investigate the combination of the anti-PD-L1 MAb (A09-246-2) and Gemcitabine (GEM). The studies were designed to explore the positioning of anti-PD-L1 therapy within the chemotherapy "holiday" period of a 21 day or 28 day cycle of GEM. Orthotopic models involve the inoculation of tumor cells into the organ of origin, resulting in a close recapitulation of disease progression as it occurs in the human setting. To create a model of pancreatic adenocarcinoma, PANC02 cells ($1 \times 10^6$) were injected into the pancreas of C57BL/6 female mice. Five days later, mice were randomized into treatment groups. GEM was dosed at 150 mg/kg in all studies and A09-246-2 was dosed at 400 µg per mouse. In two studies, a 28 day cycle of GEM was modeled (administration on days 5, 19, 26), with a 14 day holiday period during which A09-246-2 was given on days 8, 11, 14. In a third study, a 21 day cycle of GEM was modeled (administration on days 5, 12, 26, 33), with a 14 day holiday period during which A09-246-2 was given on days 13, 16, 19. Monotherapy with GEM or anti-PD-L1 failed to extend survival time in this model. However, in all three studies, the combination of GEM and A09-246-2 significantly extended mean survival time (P<0.02). Immunophenotyping revealed several effects in groups receiving A09-246-2, both as a monotherapy and in combination with GEM, that were consistent with the proposed MOA of anti-PD-L1 including increased percentages of CD8+ $T_{EM}$ in spleens, an increased ratio of splenic CD8+ $T_{EM}$ to $T_{reg}$ cells, and increased percentages of splenic PD-1+CD8+ T cells. Furthermore, immunophenotyping of tumor infiltrating lymphocytes (TIL) showed significantly increased percentages of CD8+ TIL in the combination group.

4.4 Combination with Low Dose Cyclophosphamide (CPA)

Low-dose CPA is known to enhance anti-tumor immune responses through the inhibition of immunosuppressive regulatory T cells. The potential for low-dose CPA pre-treatment was investigated to enhance the efficacy of the anti-PD-L1 Ab (A09-246-2) in the MC38 subcutaneous tumor model. Mice were inoculated subcutaneously in the right flank with $1 \times 10^6$ MC38 colon carcinoma cells. When tumors reached a mean volume of ~50 mm³, mice were sorted into treatment groups (N=14) on day 0. The combination group received 100 µg of A09-246-2 by i.v. injection on days 0, 3, and 6, with or without pre-treatment with a 100 mg/kg dose of CPA delivered i.v. on day −1. A control treatment group received 100 μg of an inactive isotype antibody in combination with CPA pretreatment. The combination treatment group demonstrated a statistically significant enhancement (p<0.050) of anti-tumor activity when compared against the isotype and monotherapy control groups. Using an ELISPOT assay, the effects of treatment on the magnitude of $CD8^+$ T cell responses directed against the well-characterized p15E tumor antigen were measured. Both CPA and A09-246-2 showed substantially increased levels of p15E-reactive $CD8^+$ T cells (~100 spots in both groups) when compared to the isotype control (~25 spots), with the combination group showing a further enhancement (~250 spots). Thus, the anti-tumor efficacy of the CPA plus A09-246-2 combination was associated with increased frequencies of tumor-antigen reactive CTL.

4.5 Combination with Cyclophosphamide/Stimuvax

The ability of PD-L1 blockade to restore anti-tumor T cell responses provides a strong rationale for combination with cancer vaccines. Stimuvax is a vaccine against the human MUC1 antigen, which is commonly overexpressed by solid tumors. Mice transgenic for the human MUC1 protein (MUC1.tg mice) are immunologically tolerant of the antigen, and, when inoculated with murine tumors that also express human MUC1, provide a relevant model of the clinical vaccination setting. In the clinic, cyclophosphamide (CPA) pre-treatment is used in combination with Stimuvax as a strategy for transiently depleting immunosuppressive $T_{reg}$ cells that can inhibit the vaccine response.

In this study, MUC1.tg mice were inoculated subcutaneously in the right rear flank with $1 \times 10^6$ MC38/MUC1 colon carcinoma cells. Five days after tumor cell inoculation, mice were randomized into treatment groups (N=10) on day −3. On day −3, a 100 mg/kg dose of CPA was administered by i.v. administration. Vaccination was initiated on day 0 and was repeated weekly. Anti-PD-L1 Ab (A09-246-2) was dosed by i.p. injection on days 0, 3, and 6. Tumors were measured twice weekly. The combination of CPA/Stimuvax and A09-246-2 demonstrated significantly enhanced (p<0.050) tumor growth inhibition when compared against treatment with CPA/Stimuvax.

In a second study, $1 \times 10^6$ PANC02/MUC1 cells were inoculated into the pancreas of MUC1.tg mice. Four days later, mice were randomized into groups (N=8) and treatment was initiated. The same treatment schedule was applied as for the first study. The combination of CPA/Stimuvax and anti-PD-L1 (A09-246-2) significantly increased mean survival time (MST) when compared against treatment with CPA/Stimuvax (MST of 43.5 days vs. 70 days, P=0.0001). Immunophenotyping by FACS showed a significant trend towards increased percentages of $CD8^+$ $T_{EM}$ and $CD8^+$ $T_{CM}$ in the combination group.

4.6 Combination with Fractionated Radiotherapy

Radiotherapy (RT) has been demonstrated to enhance the immunogenicity of tumor cells, through increased expression of MHC class I and diversification of the intracellular peptide pool. To test anti-PD-L1 antibody treatment in combination with radiotherapy, MC38 colon carcinoma cells ($1 \times 10^5$) were inoculated intramuscularly into the right quadriceps of C57BL/6 female mice. When tumors reached a mean volume of 150 mm³, mice were sorted into treatment groups (N=8) on day 0. The tumor-bearing legs were isolated and treated with 360 cGy of gamma irradiation from a cesium-137 source on days 0, 1, 2, 3, and 4 (total dose of 1800 cGy). Anti-PD-L1 Ab (A09-246-2) was dosed i.v. at 400 μg on days 3, 6, and 9. The A09-246-2 and radiotherapy combination resulted in a high rate of tumor regressions, ultimately leading to 6/10 complete responses (CR). Mice with CR were re-challenged by inoculation of MC38 tumor cells, and 3/6 mice remained tumor-free seventy-four days after the re-challenge, indicating that effective immune memory was generated by the combination therapy. Conversely, a control group treated with an isotype control antibody in combination with radiation showed significant tumor growth inhibition, but did not induce regressions.

A repeat of the RT and anti-PD-L1 (A09-246-2) combination study was performed, with the inclusion of a second combination therapy group in which the mice were systemically depleted of $CD8^+$ T cells. Additional immunological readouts measured in this study included FACS-based immunophenotyping of splenocytes, in vivo proliferation analysis, and ELISPOT assay. Again, the combination demonstrated synergistic efficacy that induced an initial phase of regression or stasis in all of the tumors. However, complete regression was only observed in ⅛ mice, with one other mouse experiencing a prolonged period of tumor stasis. Depletion of $CD8^+$ T cells completely abrogated the synergy of the combination, confirming that the mechanism involves the stimulation of anti-tumor $CD8^+$ T cell responses. This observation was further supported by increased frequencies of $CD8^+$ T cells reactive to the p15E tumor antigen. Immunophenotyping by FACS revealed increased percentages of $CD8^+$ T cell proliferation in spleens, and increased splenic percentages of $CD8^+$ $T_{EM}$ and $CD8^+$ $T_{CM}$.

4.7 Combination with Core Components of the FOLFOX Regimen

FOLFOX is a combination chemotherapy regimen, consisting of folinic acid, 5-fluorouracil (5-FU), and oxaliplatin (OX), used in the treatment of stage III colorectal cancer. The potential for combining anti-PD-L1 with the core components of FOLFOX (5-fluorouracil and oxaliplatin) in the subcutaneous MC38 colon carcinoma model were studied. Mice were inoculated in the right subcutaneous flank with $1 \times 10^6$ MC38 colon carcinoma cells. When tumors reached a mean volume of ~50 mm³, mice were sorted into treatment groups (N=10) on day 0.5-FU (60 mg/kg i.v.) and OX (5 mg/kg i.p.) were administered on days 0 and 14. Anti-PD-L1 Ab (A09-246-2) (400 μg i.v.) was given on days 3, 6, and 9. The combination treatment was observed to have significantly greater efficacy (p<0.050) when compared to A09-246-2 given alone, or 5-FU and OX given in combination with an isotype antibody. A repeat of the anti-PD-L1 Ab and FOLFOX combination study was performed and, again, the combination demonstrated significantly greater (p<0.050) anti-tumor activity than either of the monotherapy regimens. FACS-based immunophenotyping conducted in these studies revealed increases in several immunological markers consistent with a $CD8^+$ T cell driven MOA, including increased splenic levels of p15E tumor antigen specific $CD8^+$ T cells, an increase in the splenic ratio of $T_{EM}$ to regulatory T cells ($T_{reg}$), and increased splenic percentages of $CD8^*PD-1^+$ T cells. Furthermore, the percentage of tumor infiltrating natural killer (NK) cells and $CD8^+$ T cells was observed to increase significantly in the combination group.

4.8 4-Week Repeat Dose Pilot Toxicity Study in Cynomolgus Monkey

Four groups of 2 male and 2 female cynomolgus monkeys were treated with anti human PD-L1 (A09-246-2) at dose levels of 0 (vehicle), 20, 60 and 140 mg/kg by weekly intravenous infusion for total of 5 administrations.

The TK evaluation indicates that all animals were exposed to the test material throughout the study. The exposure levels increased roughly proportionally to dose increasing at both 1st and 4th dose, without any relevant accumulation or gender-dependency at any dose. Anti drug antibody were detected in 2/4 and 1/4 monkeys at 20 and 140 mg/kg levels respectively. There was no premature animal death in the study. No treatment related changes were noted in the 20 and 60 mg/kg dosing groups for all parameters evaluated in the study.

At the high dose level of 140 mg/kg, treatment related findings include slight decrease of lymphocytes in haematology testing, slight decrease in lymphocyte count together with a decrease in NK cell count on study day 30. There were no significant histological changes in major organs/tissues except moderate perivascular hemorrhage and inflammation/vessel necrosis observed at local injection site at the 140 mg/kg. There was no clear trend or change observed in multicytokine analysis at this dose level. Based on the results from this study the No Observable Adverse Effect Level (NOAEL) was identified as 140 mg/kg.

Conclusion: A09-246-2 was tolerated in cynomolgus monkey at dose levels up to 140 mg/kg after receiving a total of 5 consecutive weekly doses. Injection site reactions with moderate severity of subcutaneous/perivascular and vascular inflammatory and degenerative changes were observed at 140 mg/kg.

The invention claimed is:

1. An isolated anti-PD-L1 antibody or antigen binding fragment thereof comprising:
    (a) a heavy chain variable region; and
    (b) a light chain variable region
    comprising HVR-L1, HVR-L2 and HVR-L3 sequences, wherein:
    (i) the HVR-L1 sequence is TGTX$_7$X$_8$DVGX$_9$YNYVS (SEQ ID NO: 8); and
    (ii) the HVR-L3 sequence is SSX$_{13}$TX$_{14}$X$_{15}$X$_{16}$X$_{17}$RV (SEQ ID NO: 10); and
    wherein X$_7$ is N or S; X$_8$ is T, R or S; X$_9$ is A or G; X$_{13}$ is F or Y; X$_{14}$ is N or S; X$_{15}$ is R, T or S; X$_{16}$ is G or S; and X$_{17}$ is I or T.

2. The isolated anti-PD-L1 antibody or antigen binding fragment of claim 1, wherein the heavy chain variable region comprises HVR-H1, HVR-H2 and HVR-H3 sequences, wherein:
    (a) the HVR-H1 sequence is X$_1$YX$_2$MX$_3$ (SEQ ID NO:1);
    (b) the HVR-H2 sequence is SIYPSGGX$_4$TFYADX$_5$VKG (SEQ ID NO:2); and
    (c) the HVR-H3 sequence is IKLGTVTTVX$_6$Y (SEQ ID NO:3); and
    further wherein:
    X$_1$ is K, R, T, Q, G, A, W, M, I or S;
    X$_2$ is V, R, K, L, M or I;
    X$_3$ is H, T, N, Q, A, V, Y, W, F or M;
    X$_4$ is F or I;
    X$_5$ is S or T; and
    X$_6$ is E or D.

3. The isolated anti-PD-L1 antibody or antigen binding fragment of claim 2, wherein:
    (a) X$_1$ is M, I or S; X$_2$ is R, K, L, M or I; X$_3$ is F or M; X$_4$ is F or I; X$_5$ is S or T; X$_6$ is E or D;
    (b) X$_1$ is M, I or S; X$_2$ is L, M or I; X$_3$ is F or M; X$_4$ is I; X$_5$ S or T; X$_6$ is D; or
    (c) X$_1$ is S; X$_2$ is I; X$_3$ is M; X$_4$ is I; X$_5$ is T; X$_6$ is D.

4. The isolated anti-PD-L1 antibody or antigen binding fragment of claim 2, wherein the heavy chain variable region comprises heavy chain framework sequences HC-FR1, HC-FR2, HC-FR3 and HC-FR4 interposed between the HVR sequences, thus forming a sequence of the formula: (HC-FR1)-(HVR-H1)-(HC-FR2)-(HVR-H2)-(HC-FR3)-(HVR-H3)-(HC-FR4).

5. The isolated anti-PD-L1 antibody or antigen binding fragment of claim 4, wherein one or more of the heavy chain framework sequences is selected from:
  (a) HC-FR1 is EVQLLESGGGLVQPGGSLRLS-CAASGFTFS (SEQ ID NO:4);
  (b) HC-FR2 is WVRQAPGKGLEWVS (SEQ ID NO:5);
  (c) HC-FR3 is RFTISRDNSKNTLYLQMNSLRAED-TAVYYCAR (SEQ ID NO:6); or
  (d) HC-FR4 is WGQGTLVTVSS (SEQ ID NO:7).

6. The isolated anti-PD-L1 antibody or antigen binding fragment of claim 1, wherein:
  (a) $X_7$ is N or S; $X_8$ is T, R or S; $X_9$ is A or G; $X_{13}$ is F or Y; $X_{14}$ is S; $X_{15}$ is S; $X_{16}$ is G or S; and $X_{17}$ is T; or
  (b) $X_7$ is S; $X_8$ is S; $X_9$ is G; $X_{13}$ is Y; $X_{14}$ is S; $X_{15}$ is S; $X_{16}$ is S; and $X_{17}$ is T.

7. The isolated anti-PD-L1 antibody or antigen binding fragment of claim 2, wherein the light chain variable region comprises light chain framework sequences LC-FR1, LC-FR2, LC-FR3 and LC-FR4 interposed between the HVR sequences, thus forming a sequence of the formula: (LC-FR1)-(HVR-L1)-(LC-FR2)-(HVR-L2)-(LC-FR3)-(HVR-L3)-(LC-FR4).

8. The isolated anti-PD-L1 antibody or antigen binding fragment of claim 7, wherein one or more of the light chain framework sequences is selected from:
  (a) LC-FR1 is QSALTQPASVSGSPGQSITISC (SEQ ID NO:11);
  (b) LC-FR2 is WYQQHPGKAPKLMIY (SEQ ID NO: 12);
  (c) LC-FR3 is GVSNRFSGSKSGNTASLTISGLQAE-DEADYYC (SEQ ID NO: 13); or
  (d) LC-FR4 is FGTGTKVTVL (SEQ ID NO: 14).

9. The isolated anti-PD-L1 antibody or antigen binding fragment of claim 2, further comprising a human or murine constant domain.

10. The isolated anti-PD-L1 antibody or antigen binding fragment of claim 1, wherein:
  (a) $X_7$ is N or S; $X_8$ is T, R or S; $X_9$ is A or G; $X_{13}$ is F or Y; $X_{14}$ is S; $X_{15}$ is S; $X_{16}$ is G or S; and $X_{17}$ is T; or
  (b) $X_7$ is S; $X_8$ is S; $X_9$ is G; $X_{13}$ is Y; $X_{14}$ is S; $X_{15}$ is S; $X_{16}$ is S; and $X_{17}$ is T.

11. The isolated anti-PD-L1 antibody or antigen binding fragment of claim 1, wherein the light chain variable region comprises light chain framework sequences LC-FR1, LC-FR2, LC-FR3 and LC-FR4, interposed between the HVR sequences, thus forming a sequence of the formula: (LC-FR1)-(HVR-L1)-(LC-FR2)-(HVR-L2)-(LC-FR3)-(HVR-L3)-(LC-FR4).

12. The isolated anti-PD-L1 antibody or antigen binding fragment of claim 1, wherein the heavy chain variable region comprises an HVR-H1 comprising the amino acid sequence SYIMM (SEQ ID NO: 15), an HVR-H2 comprising the amino acid sequence SIYPSGGITFYADTVKG (SEQ ID NO: 16), and an HVR-H3 comprising the amino acid sequence IKLGTVTTVDY (SEQ ID NO: 17); and wherein the HVR-L1 comprises the amino acid sequence TGTSSDVGGYNYVS (SEQ ID NO: 18), and the HVR-L3 comprises the amino acid sequence SSYTSSSTRV (SEQ ID NO: 20).

13. The isolated anti-PD-L1 antibody or antigen binding fragment of claim 11, wherein the light chain framework sequences are selected from:
  (a) LC-FR1 is QSALTQPASVSGSPGQSITISC (SEQ ID NO:11);
  (b) LC-FR2 is WYQQHPGKAPKLMIY (SEQ ID NO: 12);
  (c) LC-FR3 is GVSNRFSGSKSGNTASLTISGLQAE-DEADYYC (SEQ ID NO: 13); or
  (d) LC-FR4 is FGTGTKVTVL (SEQ ID NO: 14).

14. The isolated anti-PD-L1 antibody or antigen binding fragment of claim 2, wherein the antibody binds to human, mouse or cynomolgus monkey PD-L1, or wherein the antibody is capable of blocking the interaction between human, mouse or cynomolgus monkey PD-L1 and the respective human, mouse or cynomolgus monkey PD-1 receptors.

* * * * *

```
                            SEQUENCE LISTING

<160> NUMBER OF SEQ ID NOS: 35

<210> SEQ ID NO 1
    <211> LENGTH: 5
    <212> TYPE: PRT
    <213> ORGANISM: Artificial Sequence
    <220> FEATURE:
    <223> OTHER INFORMATION: from human FAB library
    <220> FEATURE:
    <221> NAME/KEY: MISC_FEATURE
    <222> LOCATION: (1)..(1)
    <223> OTHER INFORMATION: X = K, R, T, Q, G, A, W, M, I or S
    <220> FEATURE:
    <221> NAME/KEY: MISC_FEATURE
    <222> LOCATION: (3)..(3)
    <223> OTHER INFORMATION: X = V, R, K, L, M or I
    <220> FEATURE:
    <221> NAME/KEY: MISC_FEATURE
    <222> LOCATION: (5)..(5)
    <223> OTHER INFORMATION: X = H, T, N, Q, A, V, Y, W, F or M

<400> SEQUENCE: 1

Xaa Tyr Xaa Met Xaa
    1               5

<210> SEQ ID NO 2
    <211> LENGTH: 17
    <212> TYPE: PRT
    <213> ORGANISM: Artificial Sequence
    <220> FEATURE:
    <223> OTHER INFORMATION: from human FAB library
    <220> FEATURE:
    <221> NAME/KEY: MISC_FEATURE
    <222> LOCATION: (8)..(8)
    <223> OTHER INFORMATION: X = F or I
    <220> FEATURE:
    <221> NAME/KEY: MISC_FEATURE
    <222> LOCATION: (14)..(14)
    <223> OTHER INFORMATION: X = S or T

<400> SEQUENCE: 2

Ser Ile Tyr Pro Ser Gly Gly Xaa Thr Phe Tyr Ala Asp Xaa Val Lys
    1               5                   10                  15

Gly

<210> SEQ ID NO 3
    <211> LENGTH: 11
    <212> TYPE: PRT
    <213> ORGANISM: Artificial Sequence
    <220> FEATURE:
    <223> OTHER INFORMATION: from human Fab library
    <220> FEATURE:
    <221> NAME/KEY: MISC_FEATURE
    <222> LOCATION: (10)..(10)
    <223> OTHER INFORMATION: X = E or D

<400> SEQUENCE: 3
```

```
Ile Lys Leu Gly Thr Val Thr Thr Val Xaa Tyr
1               5                   10

<210> SEQ ID NO 4
<211> LENGTH: 30
<212> TYPE: PRT
<213> ORGANISM: Artificial Sequence
<220> FEATURE:
<223> OTHER INFORMATION: from human Fab library

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: from human Fab library

<400> SEQUENCE: 5

Trp Val Arg Gln Ala Pro Gly Lys Gly Leu Glu Trp Val Ser
1               5                   10

<210> SEQ ID NO 6
<211> LENGTH: 32
<212> TYPE: PRT
<213> ORGANISM: Artificial Sequence
<220> FEATURE:
<223> OTHER INFORMATION: from human Fab library

<400> SEQUENCE: 6

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: from human Fab library

<400> SEQUENCE: 7

Trp Gly Gln Gly Thr Leu Val Thr Val Ser Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (4)..(4)
<223> OTHER INFORMATION: X = N or S
<220> FEATURE:
<221> NAME/KEY: MISC_FEATURE
<222> LOCATION: (5)..(5)
<223> OTHER INFORMATION: X = T, R or S
<220> FEATURE:
<221> NAME/KEY: MISC_FEATURE
```

```
<222> LOCATION: (9)..(9)
<223> OTHER INFORMATION: X = A or G

<400> SEQUENCE: 8

Thr Gly Thr Xaa Xaa Asp Val Gly Xaa Tyr Asn Tyr Val Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (1)..(1)
<223> OTHER INFORMATION: X = E or D
<220> FEATURE:
<221> NAME/KEY: MISC_FEATURE
<222> LOCATION: (3)..(3)
<223> OTHER INFORMATION: X = I, N or S
<220> FEATURE:
<221> NAME/KEY: MISC_FEATURE
<222> LOCATION: (4)..(4)
<223> OTHER INFORMATION: X = D, H or N

<400> SEQUENCE: 9

Xaa Val Xaa Xaa Arg Pro Ser
1               5

<210> SEQ ID NO 10
<211> LENGTH: 10
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (3)..(3)
<223> OTHER INFORMATION: X = F or Y
<220> FEATURE:
<221> NAME/KEY: MISC_FEATURE
<222> LOCATION: (5)..(5)
<223> OTHER INFORMATION: X = N or S
<220> FEATURE:
<221> NAME/KEY: MISC_FEATURE
<222> LOCATION: (6)..(6)
<223> OTHER INFORMATION: X = R, T or S
<220> FEATURE:
<221> NAME/KEY: MISC_FEATURE
<222> LOCATION: (7)..(7)
<223> OTHER INFORMATION: X = G or S
<220> FEATURE:
<221> NAME/KEY: MISC_FEATURE
<222> LOCATION: (8)..(8)
<223> OTHER INFORMATION: X = I or T

<400> SEQUENCE: 10

Ser Ser Xaa Thr Xaa Xaa Xaa Xaa Arg Val
1               5                   10

<210> SEQ ID NO 11
<211> LENGTH: 22
<212> TYPE: PRT
<213> ORGANISM: Artificial Sequence
<220> FEATURE:
<223> OTHER INFORMATION: from human Fab library

<400> SEQUENCE: 11

Gln Ser Ala Leu Thr Gln Pro Ala Ser Val Ser Gly Ser Pro Gly Gln
1               5                   10                  15
```

Ser Ile Thr Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: from human Fab library

<400> SEQUENCE: 12

Trp Tyr Gln Gln His Pro Gly Lys Ala Pro Lys Leu Met Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: from human Fab library

<400> SEQUENCE: 13

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: from human Fab library

<400> SEQUENCE: 14

Phe Gly Thr Gly Thr Lys Val Thr Val Leu
1               5                   10

<210> SEQ ID NO 15
<211> LENGTH: 5
<212> TYPE: PRT
<213> ORGANISM: Artificial Sequence
<220> FEATURE:
<223> OTHER INFORMATION: from human Fab library

<400> SEQUENCE: 15

Ser Tyr Ile Met Met
1               5

<210> SEQ ID NO 16
<211> LENGTH: 17
<212> TYPE: PRT
<213> ORGANISM: Artificial Sequence
<220> FEATURE:
<223> OTHER INFORMATION: from human Fab library

<400> SEQUENCE: 16

Ser Ile Tyr Pro Ser Gly Gly Ile Thr Phe Tyr Ala Asp Thr Val Lys
1               5                   10                  15

Gly

<210> SEQ ID NO 17
<211> LENGTH: 11
<212> TYPE: PRT
<213> ORGANISM: Artificial Sequence
<220> FEATURE:

```
<223> OTHER INFORMATION: from human Fab library

<400> SEQUENCE: 17

Ile Lys Leu Gly Thr Val Thr Thr Val Asp Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: from human Fab library

<400> SEQUENCE: 18

Thr Gly Thr Ser Ser Asp Val Gly Gly Tyr Asn Tyr Val Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: from human Fab library

<400> SEQUENCE: 19

Asp Val Ser Asn Arg Pro Ser
1               5

<210> SEQ ID NO 20
<211> LENGTH: 10
<212> TYPE: PRT
<213> ORGANISM: Artificial Sequence
<220> FEATURE:
<223> OTHER INFORMATION: from human Fab library

<400> SEQUENCE: 20

Ser Ser Tyr Thr Ser Ser Ser Thr Arg Val
1               5                   10

<210> SEQ ID NO 21
<211> LENGTH: 5
<212> TYPE: PRT
<213> ORGANISM: Artificial Sequence
<220> FEATURE:
<223> OTHER INFORMATION: from human Fab library

<400> SEQUENCE: 21

Met Tyr Met Met Met
1               5

<210> SEQ ID NO 22
<211> LENGTH: 17
<212> TYPE: PRT
<213> ORGANISM: Artificial Sequence
<220> FEATURE:
<223> OTHER INFORMATION: from human Fab library

<400> SEQUENCE: 22

Ser Ile Tyr Pro Ser Gly Gly Ile Thr Phe Tyr Ala Asp Ser Val Lys
1               5                   10                  15
Gly

<210> SEQ ID NO 23
<211> LENGTH: 14
<212> TYPE: PRT
<213> ORGANISM: Artificial Sequence
```

```
<220> FEATURE:
<223> OTHER INFORMATION: from human Fab library

<400> SEQUENCE: 23

Thr Gly Thr Ser Ser Asp Val Gly Ala Tyr Asn Tyr Val Ser
1               5                   10

<210> SEQ ID NO 24
<211> LENGTH: 120
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (1)..(120)
<223> OTHER INFORMATION: A09-246-2 heavy chain variable region

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 25
<211> LENGTH: 110
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (1)..(110)
<223> OTHER INFORMATION: A09-246-2 light chain variable region

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
```

<210> SEQ ID NO 26
<211> LENGTH: 120
<212> TYPE: PRT
<213> ORGANISM: Artificial Sequence
<220> FEATURE:
<223> OTHER INFORMATION: from human Fab library
<220> FEATURE:
<221> NAME/KEY: misc_feature
<222> LOCATION: (1)..(120)
<223> OTHER INFORMATION: A09-188-1 heavy chain variable region

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120
```

<210> SEQ ID NO 27
<211> LENGTH: 110
<212> TYPE: PRT
<213> ORGANISM: Artificial Sequence
<220> FEATURE:
<223> OTHER INFORMATION: from human Fab library
<220> FEATURE:
<221> NAME/KEY: MISC_FEATURE
<222> LOCATION: (1)..(110)
<223> OTHER INFORMATION: A09-188-1 light chain variable region

<400> SEQUENCE: 27

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 28
<211> LENGTH: 290
<212> TYPE: PRT

<213> ORGANISM: Homo sapiens

<400> SEQUENCE: 28

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 29
<211> LENGTH: 226
<212> TYPE: PRT
<213> ORGANISM: Artificial Sequence
<220> FEATURE:
<223> OTHER INFORMATION: from human Fab library

<400> SEQUENCE: 29

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg His His His His
    210                 215                 220

His His
225

<210> SEQ ID NO 30
<211> LENGTH: 1407
<212> TYPE: DNA
<213> ORGANISM: Artificial Sequence
<220> FEATURE:
<223> OTHER INFORMATION: from human Fab library

<400> SEQUENCE: 30

```
atggagttgc ctgttaggct gttggtgctg atgttctgga ttcctgctag ctccagcgag    60
gtgcagctgc tggaatccgg cggaggactg gtgcagcctg gcggctccct gagactgtct   120
tgcgccgcct ccggcttcac cttctccagc tacatcatga gtgtgggtgcg acaggcccct  180
ggcaagggcc tggaatgggt gtcctccatc taccctccg gcggcatcac cttctacgcc    240
gacaccgtga agggccggtt caccatctcc cgggacaact ccaagaacac cctgtacctg   300
cagatgaact ccctgcgggc cgaggacacc gccgtgtact actgcgcccg gatcaagctg   360
ggcaccgtga ccaccgtgga ctactggggc cagggcaccc tggtgacagt gtcctccgcc   420
tccaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
```

```
acgtaccgtg tggtcagcgt cctcaccgtc ctgcaccagg actggctgaa tggcaaggag      1020
tacaagtgca aggtctccaa caaagccctc ccagccccca tcgagaaaac catctccaaa      1080
gccaaagggc agccccgaga ccacaggtg  tacaccctgc ccccatcacg ggatgagctg      1140
accaagaacc aggtcagcct gacctgcctg gtcaaaggct tctatcccag cgacatcgcc      1200
gtggagtggg agagcaatgg gcagccggag aacaactaca agaccacgcc tcccgtgctg      1260
gactccgacg gctccttctt cctctatagc aagctcaccg tggacaagag caggtggcag      1320
caggggaacg tcttctcatg ctccgtgatg catgaggctc tgcacaacca ctacacgcag      1380
aagagcctct ccctgtcccc gggtaaa                                          1407
```

<210> SEQ ID NO 31
<211> LENGTH: 705
<212> TYPE: DNA
<213> ORGANISM: Artificial Sequence
<220> FEATURE:
<223> OTHER INFORMATION: from human Fab library

<400> SEQUENCE: 31

```
atggagttgc tgttaggct  gttggtgctg atgttctgga ttcctgcttc cttaagccag        60
tccgccctga cccagcctgc ctccgtgtct ggctcccctg ccagtccat  caccatcagc       120 tgcaccggca cctccagcga cgtgggcggc tacaactacg tgtcctggta tcagcagcac       180
cccggcaagg cccccaagct gatgatctac gacgtgtcca accggccctc cggcgtgtcc       240
aacagattct ccggctccaa gtccggcaac accgcctccc tgaccatcag cggactgcag       300
gcagaggacg aggccgacta ctactgctcc tcctacacct cctccagcac cagagtgttc       360
ggcaccggca caaaagtgac cgtgctgggc cagcccaagg ccaacccaac cgtgacactg       420 ttcccccat  cctccgagga actgcaggcc aacaaggcca cctggtctg  cctgatctca       480 gatttctatc caggcgccgt gaccgtggcc tggaaggctg atggctcccc agtgaaggcc       540
ggcgtggaaa ccaccaagcc ctccaagcag tccaacaaca atacgccgc  ctcctcctac       600 ctgtccctga cccccgagca gtggaagtcc caccggtcct acagctgcca ggtcacacac       660
gagggctcca ccgtggaaaa gaccgtcgcc cccaccgagt gctca                      705
```

<210> SEQ ID NO 32
<211> LENGTH: 450
<212> TYPE: PRT
<213> ORGANISM: Artificial Sequence
<220> FEATURE:
<223> OTHER INFORMATION: from human Fab library
<220> FEATURE:
<221> NAME/KEY: CHAIN
<222> LOCATION: (1)..(450)
<223> OTHER INFORMATION: A09-246-2 complete heavy chain
<220> FEATURE:
<221> NAME/KEY: CHAIN
<222> LOCATION: (1)..(30)
<223> OTHER INFORMATION: A09-246-2 heavy chain framework region 1
<220> FEATURE:
<221> NAME/KEY: CHAIN
<222> LOCATION: (1)..(120)
<223> OTHER INFORMATION: A09-246-2 heavy chain variable region
<220> FEATURE:
<221> NAME/KEY: BINDING
<222> LOCATION: (31)..(35)
<223> OTHER INFORMATION: A09-246-2 heavy chain complementarity
      determining region 1
<220> FEATURE:
<221> NAME/KEY: CHAIN
<222> LOCATION: (36)..(49)
<223> OTHER INFORMATION: A09-246-2 heavy chain framework region 2
<220> FEATURE:

```
<221> NAME/KEY: BINDING
<222> LOCATION: (50)..(66)
<223> OTHER INFORMATION: A09-246-2 heavy chain complementarity
      determining region 2
<220> FEATURE:
<221> NAME/KEY: CHAIN
<222> LOCATION: (67)..(98)
<223> OTHER INFORMATION: A09-246-2 heavy chain framework region 3
<220> FEATURE:
<221> NAME/KEY: BINDING
<222> LOCATION: (99)..(109)
<223> OTHER INFORMATION: A09-246-2 heavy chain complementarity
      determining region 3
<220> FEATURE:
<221> NAME/KEY: CHAIN
<222> LOCATION: (110)..(120)
<223> OTHER INFORMATION: A09-246-2 heavy chain framework region 4
<220> FEATURE:
<221> NAME/KEY: CHAIN
<222> LOCATION: (121)..(218)
<223> OTHER INFORMATION: A09-246-2 heavy chain constant domain 1
<220> FEATURE:
<221> NAME/KEY: CHAIN
<222> LOCATION: (219)..(233)
<223> OTHER INFORMATION: A09-246-2 hinge region
<220> FEATURE:
<221> NAME/KEY: CHAIN
<222> LOCATION: (234)..(450)
<223> OTHER INFORMATION: A09-246-2 heavy chain constant domain 2 and 3
```

<400> SEQUENCE: 32

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

-continued

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 33
<211> LENGTH: 216
<212> TYPE: PRT
<213> ORGANISM: Artificial Sequence
<220> FEATURE:
<223> OTHER INFORMATION: from human Fab library
<220> FEATURE:
<221> NAME/KEY: CHAIN
<222> LOCATION: (1)..(216)
<223> OTHER INFORMATION: A09-246-2 complete light chain
<220> FEATURE:
<221> NAME/KEY: CHAIN
<222> LOCATION: (1)..(22)
<223> OTHER INFORMATION: A09-246-2 light chain framework region 1
<220> FEATURE:
<221> NAME/KEY: CHAIN
<222> LOCATION: (1)..(110)
<223> OTHER INFORMATION: A09-246-2 light chain variable region
<220> FEATURE:
<221> NAME/KEY: BINDING
<222> LOCATION: (23)..(36)
<223> OTHER INFORMATION: A09-246-2 light chain complementarity
    determining region 1
<220> FEATURE:
<221> NAME/KEY: CHAIN
<222> LOCATION: (37)..(51)
<223> OTHER INFORMATION: A09-246-2 light chain framework region 2
<220> FEATURE:
<221> NAME/KEY: BINDING
<222> LOCATION: (52)..(58)
<223> OTHER INFORMATION: A09-246-2 light chain complementarity
    determining region 2
<220> FEATURE:
<221> NAME/KEY: CHAIN
<222> LOCATION: (59)..(90)
<223> OTHER INFORMATION: A09-246-2 light chain framework region 3
<220> FEATURE:
<221> NAME/KEY: BINDING
```

```
<222> LOCATION: (91)..(100)
<223> OTHER INFORMATION: A09-246-2 light chain complementarity
      determining region 3
<220> FEATURE:
<221> NAME/KEY: CHAIN
<222> LOCATION: (101)..(110)
<223> OTHER INFORMATION: A09-246-2 light chain framework region 4
<220> FEATURE:
<221> NAME/KEY: CHAIN
<222> LOCATION: (111)..(216)
<223> OTHER INFORMATION: A09-246-2 light chain constant domain

<400> SEQUENCE: 33
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

```
<210> SEQ ID NO 34
<211> LENGTH: 450
<212> TYPE: PRT
<213> ORGANISM: Artificial Sequence
<220> FEATURE:
<223> OTHER INFORMATION: from human Fab library
<220> FEATURE:
<221> NAME/KEY: CHAIN
<222> LOCATION: (1)..(450)
<223> OTHER INFORMATION: A09-188-1 complete heavy chain

<400> SEQUENCE: 34
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Met Trp Val Arg Gln Ala Pro Gly Lys Gly Leu Glu Trp Val
        35                  40                  45

-continued

```
Ser Ser Ile Tyr Pro Ser Gly Gly Ile Thr Phe Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Ile Tyr Tyr Cys
                 85                  90                  95
Ala Arg Ile Lys Leu Gly Thr Val Thr Thr Val Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
450
```

```
<210> SEQ ID NO 35
<211> LENGTH: 216
<212> TYPE: PRT
<213> ORGANISM: Artificial Sequence
<220> FEATURE:
<223> OTHER INFORMATION: from human Fab library
<220> FEATURE:
<221> NAME/KEY: CHAIN
<222> LOCATION: (1)..(216)
<223> OTHER INFORMATION: A09-188-1 complete light chain

<400> SEQUENCE: 35

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215
```

UNITED STATES PATENT AND TRADEMARK OFFICE
CERTIFICATE OF CORRECTION

| | |
|---|---|
| PATENT NO. | : 11,884,724 B2 |
| APPLICATION NO. | : 16/984365 |
| DATED | : February 20, 2024 |
| INVENTOR(S) | : Nastri et al. |

It is certified that error appears in the above-identified patent and that said Letters Patent is hereby corrected as shown below:

In the Claims

In Claim 3, at Column 74, Line 66, replace "I; $X_5$ S or T; $X_6$ is D; or" with --I; $X_5$ is S or T; $X_6$ is D; or--.

In Claim 6, at Column 75, Line 18, replace "fragment of claim 1, wherein:" with --fragment of claim 2, wherein:--.

Signed and Sealed this
Nineteenth Day of March, 2024

Katherine Kelly Vidal
*Director of the United States Patent and Trademark Office*